US006680182B1

(12) United States Patent
Khan et al.

(10) Patent No.: US 6,680,182 B1
(45) Date of Patent: *Jan. 20, 2004

(54) EXPRESSION OF RECOMBINANT FUSION PROTEINS IN ATTENUATED BACTERIA

(75) Inventors: Mohammed Anjam Khan, Cambridge (GB); Bernardo Villarreal-Ramos, Cambridge (GB); Carlos Estenio Hormaeche, Newcastle upon Tyne (GB); Steven Neville Chatfield, London (GB); Gordon Dougan, London (GB)

(73) Assignee: Acambis Research Limited, Slough (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/379,611

(22) PCT Filed: Jul. 30, 1993

(86) PCT No.: PCT/GB93/01617

§ 371 (c)(1), (2), (4) Date: Jul. 21, 1995

(87) PCT Pub. No.: WO94/03615

PCT Pub. Date: Feb. 17, 1994

(30) Foreign Application Priority Data

Jul. 31, 1992 (GB) ............ 9216317
Mar. 26, 1993 (GB) ............ 9306398

(51) Int. Cl.[7] ............ C12N 15/09

(52) U.S. Cl. ............ 435/69.7; 435/69.3; 424/200.1; 424/258.1; 424/93.2; 424/191.1

(58) Field of Search ............ 424/200.1, 258.1, 424/93.2, 191.1; 435/69.3, 69.7

(56) References Cited

U.S. PATENT DOCUMENTS 4,970,147 A * 11/1990 Huala et al. ............ 435/69.1
5,389,540 A * 2/1995 Makoff et al. ............ 435/69.3

(List continued on next page.)

FOREIGN PATENT DOCUMENTS

EP A-0209281 A1 1/1987
EP A-0427347 A1 5/1991

(List continued on next page.)

OTHER PUBLICATIONS

Rappuoli, Rino et al, European Journal of Gastroenterology and Hepatology, vol. 5(suppl 2), pp. S76–S78, 1993.*

(List continued on next page.)

*Primary Examiner*—Lynette R. F. Smith
*Assistant Examiner*—Ginny Allen Portner
(74) *Attorney, Agent, or Firm*—Wolf, Greenfield & Sacks, P.C.

(57) ABSTRACT

The invention provides a DNA molecule comprising a promoter sequence operably linked to a DNA sequence encoding first and second proteins linked by a hinge region wherein in that the promoter sequence can be one having activity which is induced in response to a change in the surrounding environment and the first protein can be Tetanus toxin C fragment or one or more epitopes thereof. The invention also provides intermediate molecules having a promoter operably linked to a DNA sequence encoding a first antigenic sequence and a hinge region, and at or adjacent the 3'-end thereof one or more restriction sites for the introduction of a second anti-genic sequence. In addition, the invention provides replicable expression vectors containing the DNA fusion proteins expressed therefrom, bacterial transformed with the vectors and the use of the bacteria, in vaccines.

15 Claims, 23 Drawing Sheets

U.S. PATENT DOCUMENTS

| | | | | | |
|---|---|---|---|---|---|
| 5,443,966 | A | * | 8/1995 | Fairweather et al. | 435/69.3 |
| 5,527,529 | A | * | 6/1996 | Dougan et al. | 424/258.1 |
| 5,547,664 | A | * | 8/1996 | Charles et al. | 424/93.2 |
| 5,571,694 | A | * | 11/1996 | Makoff et al. | 435/69.3 |
| 5,589,384 | A | * | 12/1996 | Lipscombe | 435/252.33 |
| 5,597,570 | A | * | 1/1997 | Sondermeyer et al. | 424/191.1 |
| 5,683,700 | A | * | 11/1997 | Charles et al. | 424/200.1 |
| 5,877,159 | A | * | 3/1999 | Powell et al. | 514/44 |
| 5,985,285 | A | * | 11/1999 | Titball et al. | 424/234.1 |
| 6,142,433 | A | * | 12/2000 | Khan et al. | 424/184.1 |
| 6,190,669 | B1 | * | 2/2001 | Noriega et al. | 424/258.1 |

FOREIGN PATENT DOCUMENTS

| | | | | |
|---|---|---|---|---|
| EP | A-0429816 | A1 | | 6/1991 |
| EP | A-0430645 | A2 | | 6/1991 |
| EP | 0 432 965 | A1 | | 6/1991 |
| WO | 8906974 | | * | 8/1989 |
| WO | WO 90/15871 | | | 12/1990 |
| WO | 9109621 | | * | 7/1991 |
| WO | WO 92/15689 | A1 | | 9/1992 |
| WO | WO 92/16557 | | | 10/1992 |
| WO | WO 94/13325 | | | 6/1994 |

OTHER PUBLICATIONS

Clements, JD et al, Res. Microbiology, vol. 141, (7–8), pp. 981–993, 1990. Vaccines against enterotoxigenic bacterial pathogens based on hybrid Salmonella that express heterologous antigens.*

Oxer, MD et al. Jun. 11, 1991, vol. 19(11), p. 2889–92, (abs.) Nucleic Acids Res.*

Chatfield S.N et al, Biotechnology, vol. 10(8), Aug. 1992, pp. 888–892 (abs).*

Auriault, C. et al., The J. Immunol., vol. 141(5), Sep. 1, 1988, pp. 1687–1694.*

Bell, AI et al, Molecular Microbiol., 1990, vol. 4(10) pp. 1753–1763.*

Choo, Viuren, Lancet, vol. 344(8927), Oct. 1, 1994, pp. 945–946.*

Chatfield, SN et al, Vaccine, Dec. 1989, vol. 7(6), p. 495–8.*

El–Ghorae, NM et al, J. of Eqyption Society of Parasitology, vol. 22(3), pp. 747–765, 1992.*

Fair Weather NF et al, Res. Microbiol, 1990, Sep.–Oct. vol. 141(7–8), pp. 769–773.*

Goldman, BS et al, 91st general Meeting of The Am. Soc. Sol. Microbiol., May 5–9, 1991, p. 229,# K87 vol91(0).*

Griffin, H.G., World Poultry Sci, vol. 47(2), 1991, pp. 129–140.*

Jayaraman, PS et al, vol. 17(1), 1989, Nucleic Acids Rs., pp. 135–145.*

Jayaraman, PS et al, Molecular Microbiol, 1988, vol. 2(4), pp. 527–530, 1988.*

Lipscombe, M et al, Molecular Microbiol, 1991, vol. 5(6), pp. 1385–1392, Jun.*

Maquire, T et al, 1993, pp. 142–145, Proceedings of the Sixth Symposoium on Arborvirus Res. in Australia.*

Mahoff et al, Bio/Technology, vol. 7 pp. 1043–1045, Oct. 1989.*

Schodel, E et al, Vaccine, vol. 11(2), 1993, pp. 143–148.*

Spiro, S. et al, FEMS Microbiol Rev., Aug. 1990, vol. 6(4), pp. 399–428.*

Strugnell, RA et al, Gene, Mar. 30, 1990, vol. 88(1), pp. 57–63.*

Tite, JP et al, Immunol. Aug. 1990, vol. 70(4), pp. 540–546.*

Wu, Jer–Yuarn et al, J. of Bacteriol;. Jan. 1991, vol. 173 (1), pp. 325–333.*

Schutze et al., (1985) J. Immunology 135, 2319–22.

Muller et al., (1982) P.N.A.S. USA 79, 569–73.

Hudson et al., (1993) J. Am. Chem. Soc. 115, 2119–24.

Francis et al., Nature, 1987, vol. 330, pp. 168–170.

* cited by examiner

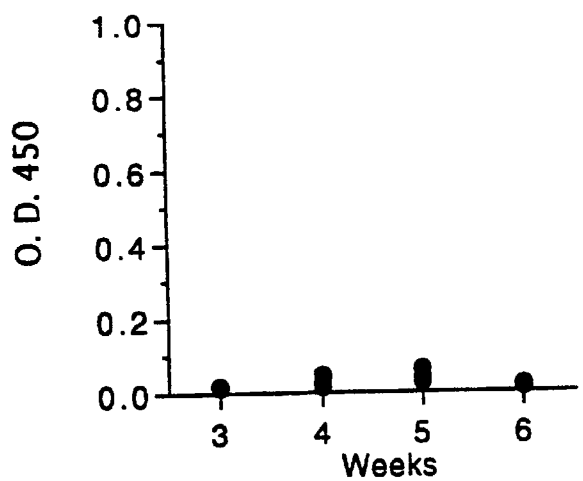
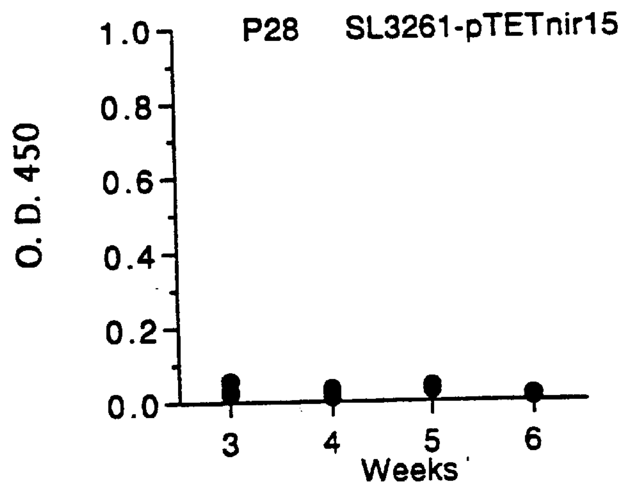
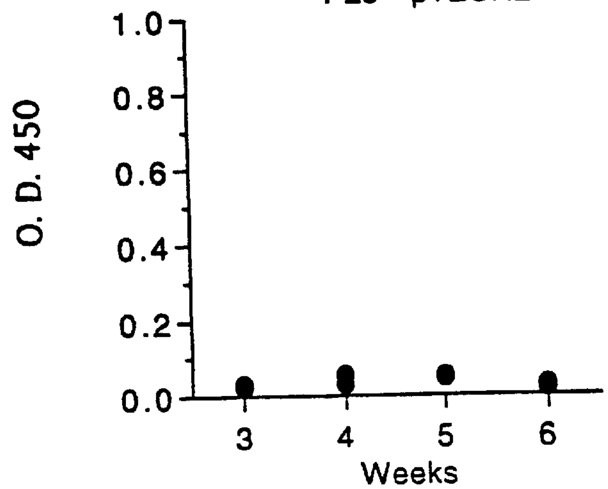
Figure 5

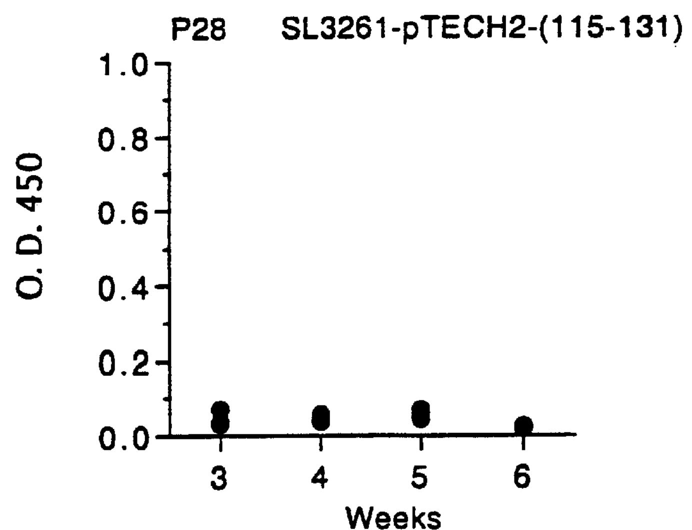
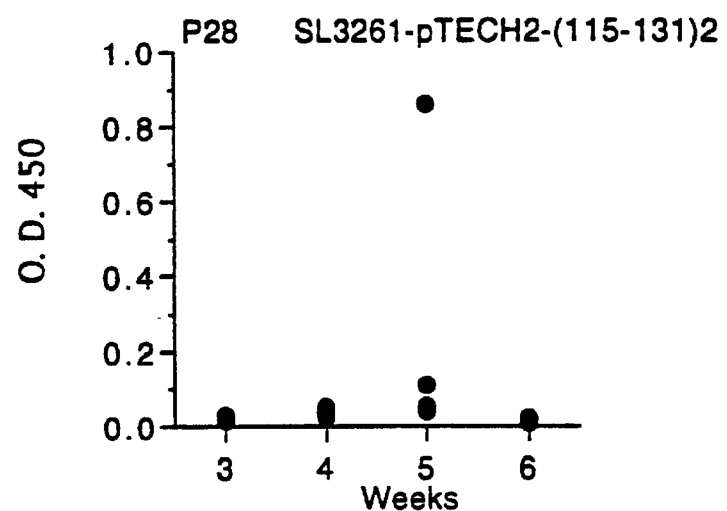
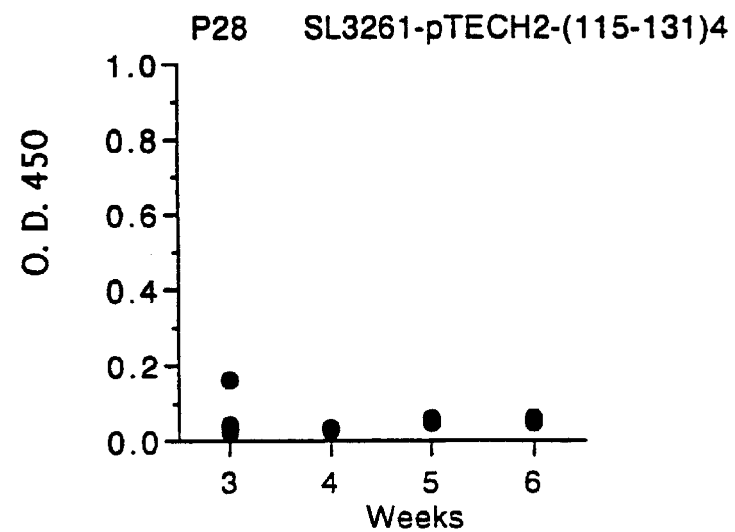
Figure 5 continued

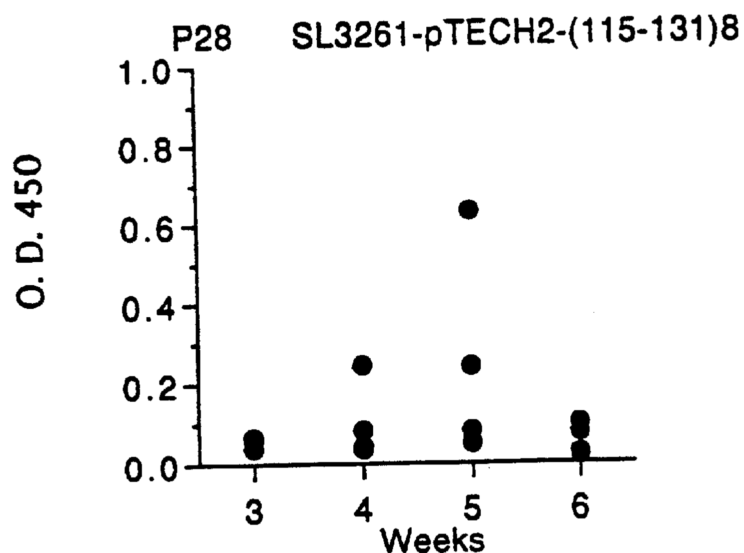
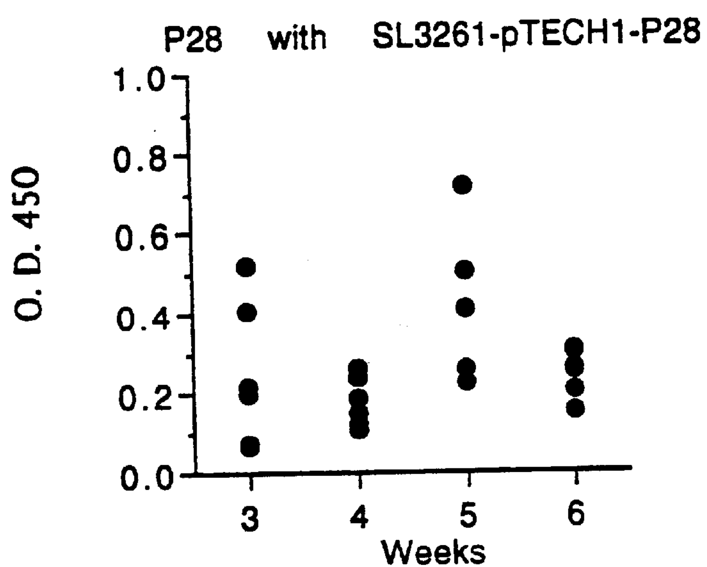
Figure 5 continued

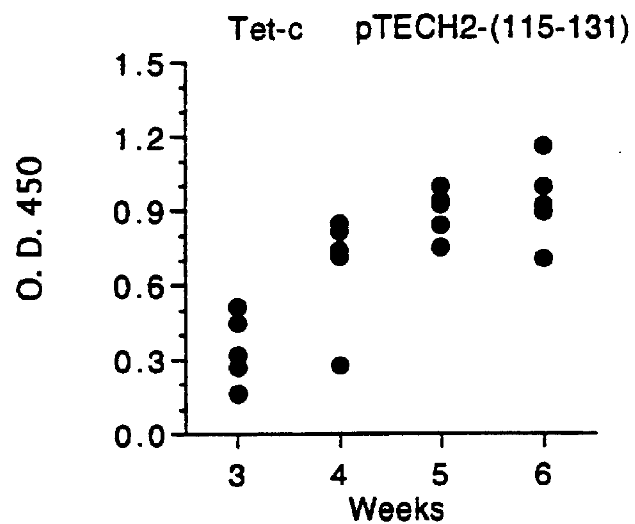
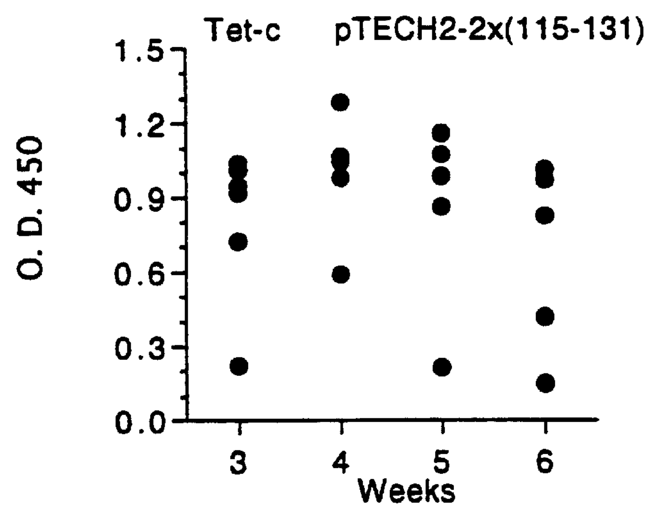
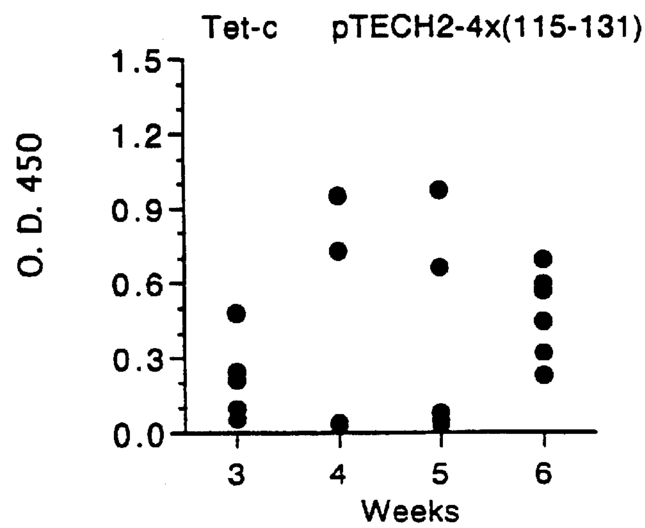
Figure 6 continued

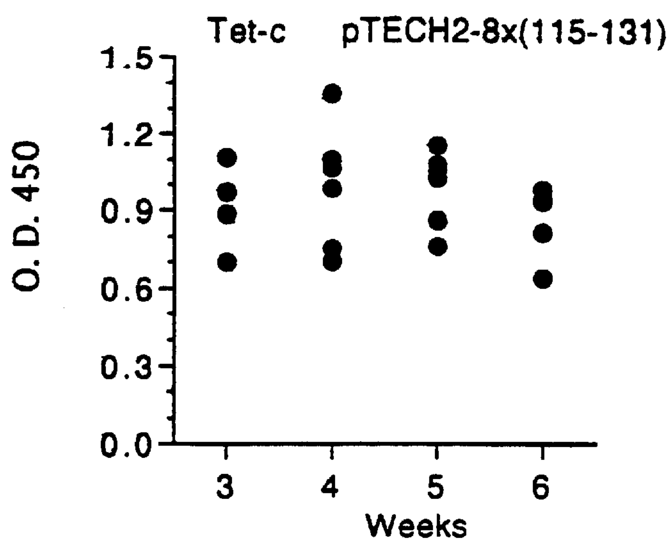
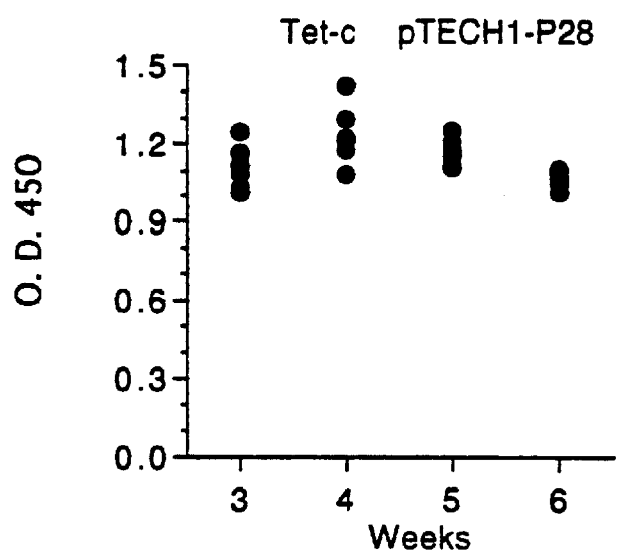
Figure 6 continued

THE CONSTRUCTS

Examples of Heteromers

TET C

TET C

= S. mansoni P28 epitope

= SIV gp 120 V2 epitope

= Hinge

DNA Sequence of the Vector pTECH1

(SEQ ID NO: 17)

1bp -TTCAGGTAAATTTGATGTACATCAAATGGTACCCCTTGCTGAATCGTTAAGGTAGGCGGT - 60bp

AGGGCCCAGATCTTAATCATCCACAGGAGACTTTCTGATGAAAAACCTTGATTGTTGGGT

CGACAACGAAGAAGACATCGATGTTATCCTGAAAAAGTCTACCATTCTGAACTTGGACAT

CAACAACGATATTATCTCCGACATCTCTGGTTTCAACTCCTCTGTTATCACATATCCAGA

TGCTCAATTGGTGCCGGGCATCAACGGCAAAGCTATCCACCTGGTTAACAACGAATCTTC

TGAAGTTATCGTGCACAAGGCCATGGACATCGAATACAACGACATGTTCAACAACTTCAC

CGTTAGCTTCTGGCTGCGCGTTCCGAAAGTTTCTGCTTCCCACCTGGAACAGTACGGCAC

TAACGAGTACTCCATCATCAGCTCTATGAAGAAACACTCCCTGTCCATCGGCTCTGGTTG

GTCTGTTTCCCTGAAGGGTAACAACCTGATCTGGACTCTGAAAGACTCCGCGGGCGAAGT

TCGTCAGATCACTTTCCGCGACCTGCCGGACAAGTTCAACGCGTACCTGGCTAACAAATG

GGTTTTCATCACTATCACTAACGATCGTCTGTCTTCTGCTAACCTGTACATCAACGGCGT

TCTGATGGGCTCCGCTGAAATCACTGGTCTGGGCGCTATCCGTGAGGACAACAACATCAC

TCTTAAGCTGGACCGTTGCAACAACAACAACCAGTACGTATCCATCGACAAGTTCCGTAT

CTTCTGCAAAGCACTGAACCCGAAAGAGATCGAAAAACTGTATACCAGCTACCTGTCTAT

CACCTTCCTGCGTGACTTCTGGGGTAACCCGCTGCGTTACGACACCGAATATTACCTGAT

CCCGGTAGCTTCTAGCTCTAAAGACGTTCAGCTGAAAAACATCACTGACTACATGTACCT

GACCAACGCGCCGTCCTACACTAACGGTAAACTGAACATCTACTACCGACGTCTGTACAA

CGGCCTGAAATTCATCATCAAACGCTACACTCCGAACAACGAAATCGATTCTTTCGTTAA

ATCTGGTGACTTCATCAAACTGTACGTTTCTTACAACAACAACGAACACATCGTTGGTTA

CCCGAAAGACGGTAACGCTTTCAACAACCTGGACAGAATTCTGCGTGTTGGTTACAACGC

TCCGGGTATCCCGCTGTACAAAAAAATGGAAGCTGTTAAACTGCGTGACCTGAAAACCTA

CTCTGTTCAGCTGAAACTGTACGACGACAAAAACGCTTCTCTGGGTCTGGTTGGTACCCA

CAACGGTCAGATCGGTAACGACCCGAACCGTGACATCCTGATCGCTTCTAACTGGTACTT

CAACCACCTGAAAGACAAAATCCTGGGTTGCGACTGGTACTTCGTTCCGACCGATGAAGG

TTGGACCAACGACGGGCCGGGGCCCTCTAGAATCACTAGTTAAGGATCCGCTAGCCCGCC

Figure 12 (2 of 3)

pTECH1 DNA Sequence continued

TAATGAGCGGGCTTTTTTTTCTCGGGCAGCGTTGGGTCCTGGCCACGGGTGCGCATGATC

GTGCTCCTGTCGTTGAGGACCCGGCTAGGCTGGCGGGGTTGCCTTACTGGTTAGCAGAAT

GAATCACCGATACGCGAGCGAACGTGAAGCGACTGCTGCTGCAAAACGTCTGCGACCTGA

GCAACAACATGAATGGTCTTCGGTTTCCGTGTTTCGTAAAGTCTGGAAACGCGGAAGTCA

GCGCTCTTCCGCTTCCTCGCTCACTGACTCGCTGCGCTCGGTCGTTCGGCTGCGGCGAGC

GGTATCAGCTCACTCAAAGGCGGTAATACGGTTATCCACAGAATCAGGGGATAACGCAGG

AAAGAACATGTGAGCAAAAGGCCAGCAAAAGGCCAGGAACCGTAAAAAGGCCGCGTTGCT

GGCGTTTTTCCATAGGCTCCGCCCCCCTGACGAGCATCACAAAAATCGACGCTCAAGTCA

GAGGTGGCGAAACCCGACAGGACTATAAAGATACCAGGCGTTTCCCCCTGGAAGCTCCCT

CGTGCGCTCTCCTGTTCCGACCCTGCCGCTTACCGGATACCTGTCCGCCTTTCTCCCTTC

GGGAAGCGTGGCGCTTTCTCAATGCTCACGCTGTAGGTATCTCAGTTCGGTGTAGGTCGT

TCGCTCCAAGCTGGGCTGTGTGCACGAACCCCCCGTTCAGCCCGACCGCTGCGCCTTATC

CGGTAACTATCGTCTTGAGTCCAACCCGGTAAGACACGACTTATCGCCACTGGCAGCAGC

CACTGGTAACAGGATTAGCAGAGCGAGGTATGTAGGCGGTGCTACAGAGTTCTTGAAGTG

GTGGCCTAACTACGGCTACACTAGAAGGACAGTATTTGGTATCTGCGCTCTGCTGAAGCC

AGTTACCTTCGGAAAAAGAGTTGGTAGCTCTTGATCCGGCAAACAAACCACCGCTGGTAG

CGGTGGTTTTTTTGTTTGCAAGCAGCAGATTACGCGCAGAAAAAAAGGATCTCAAGAAGA

TCCTTTGATCTTTTCTACGGGGTCTGACGCTCAGTGGAACGAAAACTCACGTTAAGGGAT

TTTGGTCATGAGATTATCAAAAAGGATCTTCACCTAGATCCTTTTAAATTAAAAATGAAG

TTTTAAATCAATCTAAAGTATATATGAGTAAACTTGGTCTGACAGTTACCAATGCTTAAT

CAGTGAGGCACCTATCTCAGCGATCTGTCTATTTCGTTCATCCATAGTTGCCTGACTCCC

CGTCGTGTAGATAACTACGATACGGGAGGGCTTACCATCTGGCCCCAGTGCTGCAATGAT

ACCGCGAGACCCACGCTCACCGGCTCCAGATTTATCAGCAATAAACCAGCCAGCCGGAAG

GGCCGAGCGCAGAAGTGGTCCTGCAACTTTATCCGCCTCCATCCAGTCTATTAATTGTTG

Figure 12 (3 of 3)

pTECH1 DNA Sequence continued

CCGGGAAGCTAGAGTAAGTAGTTCGCCAGTTAATAGTTTGCGCAACGTTGTTGCCATTGC

TGCAGGCATCGTGGTGTCACGCTCGTCGTTTGGTATGGCTTCATTCAGCTCCGGTTCCCA

ACGATCAAGGCGAGTTACATGATCCCCCATGTTGTGCAAAAAAGCGGTTAGCTCCTTCGG

TCCTCCGATCGTTGTCAGAAGTAAGTTGGCCGCAGTGTTATCACTCATGGTTATGGCAGC

ACTGCATAATTCTCTTACTGTCATGCCATCCGTAAGATGCTTTTCTGTGACTGGTGAGTA

CTCAACCAAGTCATTCTGAGAATAGTGTATGCGGCGACCGAGTTGCTCTTGCCCGGCGTC

AACACGGGATAATACCGCGCCACATAGCAGAACTTTAAAAGTGCTCATCATTGGAAAACG

TTCTTCGGGGCGAAAACTCTCAAGGATCTTACCGCTGTTGAGATCCAGTTCGATGTAACC

CACTCGTGCACCCAACTGATCTTCAGCATCTTTTACTTTCACCAGCGTTTCTGGGTGAGC

AAAAACAGGAAGGCAAAATGCCGCAAAAAAGGGAATAAGGGCGACACGGAAATGTTGAAT

ACTCATACTCTTCCTTTTTCAATATTATTGAAGCATTTATCAGGGTTATTGTCTCATGAG

CGGATACATATTTGAATGTATTTAGAAAAATAAACAAATAGGGGTTCCGCGCACATTTCC

CCGAAAAGTGCCACCTGACGTCTAAGAAACCATTATTATCATGACATTAACCTATAAAAA

TAGGCGTATCACGAGGCCCTTTCGTCTTCAAGAA - 3754bp

Figure 13 (1 of 3)

DNA Sequence of the Vector pTECH2

(SEQ ID NO: 18)

1bp - TTCAGGTAAATTTGATGTACATCAAATGGTACCCCTTGCTGAATCGTTAAGGTAGGCGGT - 60bp

AGGGCCCAGATCTTAATCATCCACAGGAGACTTTCTGATGAAAAACCTTGATTGTTGGGT

CGACAACGAAGAAGACATCGATGTTATCCTGAAAAAGTCTACCATTCTGAACTTGGACAT

CAACAACGATATTATCTCCGACATCTCTGGTTTCAACTCCTCTGTTATCACATATCCAGA

TGCTCAATTGGTGCCGGGCATCAACGGCAAAGCTATCCACCTGGTTAACAACGAATCTTC

TGAAGTTATCGTGCACAAGGCCATGGACATCGAATACAACGACATGTTCAACAACTTCAC

CGTTAGCTTCTGGCTGCGCGTTCCGAAAGTTTCTGCTTCCCACCTGGAACAGTACGGCAC

TAACGAGTACTCCATCATCAGCTCTATGAAGAAACACTCCCTGTCCATCGGCTCTGGTTG

GTCTGTTTCCCTGAAGGGTAACAACCTGATCTGGACTCTGAAAGACTCCGCGGGCGAAGT

TCGTCAGATCACTTTCCGCGACCTGCCGGACAAGTTCAACGCGTACCTGGCTAACAAATG

GGTTTTCATCACTATCACTAACGATCGTCTGTCTTCTGCTAACCTGTACATCAACGGCGT

TCTGATGGGCTCCGCTGAAATCACTGGTCTGGGCGCTATCCGTGAGGACAACAACATCAC

TCTTAAGCTGGACCGTTGCAACAACAACAACCAGTACGTATCCATCGACAAGTTCCGTAT

CTTCTGCAAAGCACTGAACCCGAAAGAGATCGAAAAACTGTATACCAGCTACCTGTCTAT

CACCTTCCTGCGTGACTTCTGGGGTAACCCGCTGCGTTACGACACCGAATATTACCTGAT

CCCGGTAGCTTCTAGCTCTAAAGACGTTCAGCTGAAAAACATCACTGACTACATGTACCT

GACCAACGCGCCGTCCTACACTAACGGTAAACTGAACATCTACTACCGACGTCTGTACAA

CGGCCTGAAATTCATCATCAAACGCTACACTCCGAACAACGAAATCGATTCTTTCGTTAA

ATCTGGTGACTTCATCAAACTGTACGTTTCTTACAACAACAACGAACACATCGTTGGTTA

CCCGAAAGACGGTAACGCTTTCAACAACCTGGACAGAATTCTGCGTGTTGGTTACAACGC

TCCGGGTATCCCGCTGTACAAAAAAATGGAAGCTGTTAAACTGCGTGACCTGAAAACCTA

CTCTGTTCAGCTGAAACTGTACGACGACAAAAACGCTTCTCTGGGTCTGGTTGGTACCCA

CAACGGTCAGATCGGTAACGACCCGAACCGTGACATCCTGATCGCTTCTAACTGGTACTT

CAACCACCTGAAAGACAAAATCCTGGGTTGCGACTGGTACTTCGTTCCGACCGATGAAGG

TTGGACCAACGACGGGCCGGGGCCCTCTAGAGGATCCGATATCAAGCTTACTAGTTAATG

ATCCGCTAGCCCGCCTAATGAGCGGGCTTTTTTTTCTCGGGCAGCGTTGGGTCCTGGCCA

CGGGTGCGCATGATCGTGCTCCTGTCGTTGAGGACCCGGCTAGGCTGGCGGGGTTGCCTT

Figure 13 (2 of 3)

pTECH2 DNA Sequence continued

ACTGGTTAGCAGAATGAATCACCGATACGCGAGCGAACGTGAAGCGACTGCTGCTGCAAA

ACGTCTGCGACCTGAGCAACAACATGAATGGTCTTCGGTTTCCGTGTTTCGTAAAGTCTG

GAAACGCGGAAGTCAGCGCTCTTCCGCTTCCTCGCTCACTGACTCGCTGCGCTCGGTCGT

TCGGCTGCGGCGAGCGGTATCAGCTCACTCAAAGGCGGTAATACGGTTATCCACAGAATC

AGGGGATAACGCAGGAAAGAACATGTGAGCAAAAGGCCAGCAAAAGGCCAGGAACCGTAA

AAAGGCCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGCGTTTCC

CCCTGGAAGCTCCCTCGTGCGCTCTCCTGTTCCGACCCTGCCGCTTACCGGATACCTGTC

CGCCTTTCTCCCTTCGGGAAGCGTGGCGCTTTCTCAATGCTCACGCTGTAGGTATCTCAG

TTCGGTGTAGGTCGTTCGCTCCAAGCTGGGCTGTGTGCACGAACCCCCCGTTCAGCCCGA

CCGCTGCGCCTTATCCGGTAACTATCGTCTTGAGTCCAACCCGGTAAGACACGACTTATC

GCCACTGGCAGCAGCCACTGGTAACAGGATTAGCAGAGCGAGGTATGTAGGCGGTGCTAC

AGAGTTCTTGAAGTGGTGGCCTAACTACGGCTACACTAGAAGGACAGTATTTGGTATCTG

CGCTCTGCTGAAGCCAGTTACCTTCGGAAAAAGAGTTGGTAGCTCTTGATCCGGCAAACA

AACCACCGCTGGTAGCGGTGGTTTTTTTGTTTGCAAGCAGCAGATTACGCGCAGAAAAAA

AGGATCTCAAGAAGATCCTTTGATCTTTTCTACGGGGTCTGACGCTCAGTGGAACGAAAA

CTCACGTTAAGGGATTTTGGTCATGAGATTATCAAAAAGGATCTTCACCTAGATCCTTTT

AAATTAAAAATGAAGTTTTAAATCAATCTAAAGTATATATGAGTAAACTTGGTCTGACAG

TTACCAATGCTTAATCAGTGAGGCACCTATCTCAGCGATCTGTCTATTTCGTTCATCCAT

AGTTGCCTGACTCCCCGTCGTGTAGATAACTACGATACGGGAGGGCTTACCATCTGGCCC

CAGTGCTGCAATGATACCGCGAGACCCACGCTCACCGGCTCCAGATTTATCAGCAATAAA

CCAGCCAGCCGGAAGGGCCGAGCGCAGAAGTGGTCCTGCAACTTTATCCGCCTCCATCCA

GTCTATTAATTGTTGCCGGGAAGCTAGAGTAAGTAGTTCGCCAGTTAATAGTTTGCGCAA

CGTTGTTGCCATTGCTGCAGGCATCGTGGTGTCACGCTCGTCGTTTGGTATGGCTTCATT

CAGCTCCGGTTCCCAACGATCAAGGCGAGTTACATGATCCCCCATGTTGTGCAAAAAAGC

GGTTAGCTCCTTCGGTCCTCCGATCGTTGTCAGAAGTAAGTTGGCCGCAGTGTTATCACT

CATGGTTATGGCAGCACTGCATAATTCTCTTACTGTCATGCCATCCGTAAGATGCTTTTC

Figure 13 (3 of 3)

pTECH2 DNA Sequence continued

TGTGACTGGTGAGTACTCAACCAAGTCATTCTGAGAATAGTGTATGCGGCGACCGAGTTG

CTCTTGCCCGGCGTCAACACGGGATAATACCGCGCCACATAGCAGAACTTTAAAAGTGCT

CATCATTGGAAAACGTTCTTCGGGGCGAAAACTCTCAAGGATCTTACCGCTGTTGAGATC

CAGTTCGATGTAACCCACTCGTGCACCCAACTGATCTTCAGCATCTTTTACTTTCACCAG

CGTTTCTGGGTGAGCAAAAACAGGAAGGCAAAATGCCGCAAAAAAGGGAATAAGGGCGAC

ACGGAAATGTTGAATACTCATACTCTTCCTTTTTCAATATTATTGAAGCATTTATCAGGG

TTATTGTCTCATGAGCGGATACATATTTGAATGTATTTAGAAAAATAAACAAATAGGGGT

TCCGCGCACATTTCCCCGAAAAGTGCCACCTGACGTCTAAGAAACCATTATTATCATGAC

ATTAACCTATAAAAATAGGCGTATCACGAGGCCCTTTCGTCTTCAAGAA

```
                   XbaI    BamHi   EcoRV   HindIII SpeI    Stop BamHi
---HINGE----       TCTAGA  GGATCC  GATATC  AAGCTT  ACTAGT  TAA  TGATC
                   AGATCT  CCTAGG  CTATAG  TTCGAA  TGATCA  ATT  ACTAG
                              (SEQ ID NO: 19)

---GPGP ----          S  R  G  S  D  I  K  L  T  S  *

                              (SEQ ID NO: 20)
```

EXPRESSION OF RECOMBINANT FUSION PROTEINS IN ATTENUATED BACTERIA

This invention relates to DNA constructs, replicable expression vectors containing the constructs, attenuated bacteria containing the constructs and vaccines containing the said bacteria.

In recent years, there has emerged a new generation of live oral salmonella vaccines based upon strains of Salmonella which have been attenuated by the introduction of a non-reverting mutation in a gene in the aromatic biosynthetic pathway of the bacterium. Such strains are disclosed, for example, in EP-A-0322237. The aforesaid live oral salmonella vaccines are showing promise as vaccines for salmonellosis in man and animals, and they can also be used effectively as carriers for the delivery of heterologous antigens to the immune system. Combined salmonella vaccines have been used to deliver antigens from viruses, bacteria, and parasites, eliciting secretory, humoral and cell-mediated immune responses to the recombinant antigens. Combined salmonella vaccines show great potential as single dose oral multivaccine delivery systems [C. Hormaeche et al, FEMS Symposium No. 63, Plenum, New York; pp 71–83, 1992].

There are problems to be overcome in the development of combined salmonella vaccines. A major consideration is obtaining a high level of expression of the recombinant antigen in the salmonella vaccine so that it will be sufficient to trigger an immune response. However, unregulated high level expression of foreign antigens can be toxic and affect cell viability [I. Charles and G. Dougan, TIBTECH 8, pp 117–21, 1990], rendering the vaccine ineffective or causing loss of the recombinant DNA. Several possible solutions to this problem have been described, such as expression from plasmids carrying essential genes, "on-off" promoters or incorporation of the foreign genes into the salmonella chromosome.

An alternative approach to overcoming the aforesaid problem would be to use a promoter which is inducible in vivo, and one such promoter is the *E. coli* nitrite reductase promoter nirB which is induced under anaerobiosis and has been used in biotechnology for the production of tetanus toxin fragment C (TetC) of *Clostridium tetani* [M. D. Oxer et al Nucl. Ac. Res., 19, pp 2889–92, 1991]. It has previously been found by the inventors of this application (S. N. Chatfield et al Bio/Technology, Vol. 10, pp 888–92 1992) that an Aro Salmonella harbouring a construct expressing TetC from the nirB promoter (pTETnir15) elicited very high anti-tetanus antibody responses in mice. The article by Chatfield et al was published after the priority date of this application.

However, we have also found that when it was attempted to express the P28 antigen from *Schistosoma mansoni* alone from nirB, the resulting construct was not immunogenic.

Tetanus toxoid has been extensively used as an adjuvant for chemically coupled guest epitopes [D. A. Herrington et al. Nature, 328, pp 257–9 1987]. The potent immunogenicity of TetC in Salmonella suggested to us that it may be possible to exploit this character to promote the immune response of the guest peptides or proteins. However, fusing two proteins together often leads to an incorrectly folded chimaeric protein which no longer retains the properties of the individual components. For example the B subunit of the *Vibrio cholerae* (CT-B) and *E. coli* (LT-B) enterotoxins are powerful mucosal immunogens but genetic fusions to these subunits can alter the structure and properties of the carrier and hence their immunogenicity [see M. Sandkvist et al. J. Bacteriol 169, pp 4570–6, 1987, Clements 1990 and M. Lipscombe et al [Mol. Microbiol 5, pp 1385 1990]. Moreover, many heterologous genes expressed in bacteria are not produced in soluble properly folded, or active forms and tend to accumulate as insoluble aggregates [see C. Schein et al. Bio/Technology 6, pp 291–4, 1988 and R. Halenbeck et al; Bio/Technology 7, pp 710–5, 19893.

It is an object of the invention to overcome the aforementioned problems.

We have now found that efficient expression of recombinant antigens, and in particular fusion proteins, can be achieved in bacteria such as salmonellae, by the use of an inducible promoter such as nirB and by incorporating a flexible hinge region between two antigenic components of the fusion protein. The resulting recombinant antigens have been shown to have good immunogenicity. It has also been found, surprisingly, that enhanced expression of a protein can be obtained when a gene coding for the protein is linked to the gene for tetanus toxin C fragment.

Accordingly, in a first aspect, the present invention provides a DNA construct comprising a promoter sequence operably linked to a DNA sequence encoding first and second proteins linked by a hinge region, characterised in that the promoter sequence is one having activity which is induced in response to a change in the surrounding environment.

In another aspect, the invention provides a DNA construct comprising a promoter sequence operably linked to a DNA sequence encoding linked first and second proteins, wherein the first heterologous protein is an antigenic sequence comprising tetanus toxin fragment C or one or more epitopes thereof.

In a further aspect, the invention provides a replicable expression vector, suitable for use in bacteria, containing a DNA construct as hereinbefore defined. In a another aspect, the invention provides a fusion protein, preferably in substantially pure form, the fusion protein comprising linked (e.g. by a hinge region) first and second proteins, the fusion protein being expressed by a replicable expression vector as hereinbefore defined.

In a further aspect the invention provides a process for the preparation of an attenuated bacterium which comprises transforming an attenuated bacterium with a DNA construct as hereinbefore defined.

The invention also provides a vaccine composition comprising an attenuated bacterium, or a fusion protein, as hereinbefore defined, and a pharmaceutically acceptable carrier.

The first and second proteins are preferably heterologous proteins and in particular can be polypeptide immunogens; for example they may be antigenic sequences derived from a virus, bacterium, fungus, yeast or parasite. In particular, it is preferred that the first said protein is an antigenic sequence comprising tetanus toxin fragment C or epitopes thereof.

The second protein is preferably an antigenic determinant of a pathogenic organism. For example, the antigenic determinant may be an antigenic sequence derived from a virus, bacterium, fungus, yeast or parasite.

Examples of viral antigenic sequences for the first and/or second heterologous proteins are sequences derived from a type of human immuno-deficiency virus (HIV) such as HIV-1 or HIV-2, the CD4 receptor binding site from HIV, for example from HIV-1 or -2., hepatitis A or B virus, human rhinovirus such as type 2 or type 14, Herpes simplex virus, poliovirus type 2 or 3, foot-and-mouth disease virus (FMDV), rabies virus, rotavirus, influenza virus, coxsackie virus, human papilloma virus (HPV), for example the type 16 papilloma virus, the E7 protein thereof, and fragments containing the E7 protein or its epitopes; and simian immunodeficiency virus (SIV). Examples of antigens derived from bacteria are those derived from *Bordetella pertussis* (e.g. P69 protein and filamentous haemagglutinin (FHA) antigens), *Vibrio cholerae, Bacillus anthracis*, and *E. coli* antigens such as *E. coli* heat Labile toxin B subunit (LT-B), *E. coli* K88 antigens, and enterotoxigenic *E. coli* antigens. Other examples of antigens include the cell surface antigen CD4, *Schistosoma mansoni* P28 glutathione S-transferase antigens (P28 antigens) and antigens of flukes, mycoplasma, roundworms, tapeworms, *Chlamydia trachomatis*, and malaria parasites, eg. parasites of the genus plasmodium or babesia, for example *Plasmodium falciparum*, and peptides encoding immunogenic epitopes from the aforementioned antigens.

Particular antigens include the full length *Schistosoma mansoni* P28, and oligomers (e.g. 2, 4 and 8-mers) of the immunogenic P28 aa 115–131 peptide (which contains both a B and T cell epitope), and human papilloma virus E7 protein, Herpes simplex antigens, foot and mouth disease virus antigens and simian immunodeficiency virus antigens.

The promoter sequence is one having activity which is induced in response to a change in the surrounding environment, and an example of such a promoter sequence is one which has activity which is induced by anaerobic conditions. A particular example of such a promoter sequence is the nirB promoter which has been described, for example in International Patent Application PCT/GB92/00387. The nirB promoter has been isolated from *E. coli*, where it directs expression of an operon which includes the nitrite reductase gene nirB (Jayaraman et al, J. Mol. Biol. 196, 781–788, 1987), and nirD, nirC, cysG (Peakman et al, Eur. J. Biochem. 191, 315–323, 1990). It is regulated both by nitrite and by changes in the oxygen tension of the environment, becoming active when deprived of oxygen, (Cole, Biochem, Biophys. Acta. 162, 356–368, 1968). Response to anaerobiosis is mediated through the protein FNR, acting as a transcriptional activator, in a mechanism common to many anaerobic respiratory genes. By deletion and mutational analysis the part of the promoter which responds solely to anaerobiosis has been isolated and by comparison with other anaerobically-regulated promoters a consensus FNR-binding site has been identified (Bell et al, Nucl, Acids. Res. 17, 3865–3874, 1989; Jayaraman et al, Nucl, Acids, Res. 17, 135–145, 1989). It has also been shown that the distance between the putative FNR-binding site and the −10 homology region is critical (Bell et al, Molec. Microbiol.4, 1753–1763, 1990). It is therefore preferred to use only that part of the nirB promoter which responds solely to anaerobiosis. As used herein, references to the nirB promoter refer to the promoter itself or a part or derivative thereof which is capable of promoting expression of a coding sequence under anaerobic conditions. The preferred sequence, and which contains the nirB promoter is: AATTCAGGTAAATTTGATGTACAT-CAAATGGTACCCCTTGCTGAATCGTTAAGG TAG-GCGGTAGGGCC (SEQ ID NO: 1)

The hinge region is a region designed to promote the independent folding of both the first and second proteins by providing both spatial and temporal separation between the domains.

The hinge region typically is a sequence encoding a high proportion of proline and/or glycine amino acids. The hinge region may be composed entirely of proline and/or glycine amino acids. The hinge region may comprise one or more glycine-proline dipeptide units.

The hinge region may, for example, contain up to about fifteen amino acids, for example at least 4 and preferably 6–14 amino acids, the number of amino acids being such as to impart flexibility between the first and second proteins.

In one embodiment, the hinge region can correspond substantially to the hinge domain of an antibody immunoglobulin. The hinge regions of IgG antibodies in particular are rich in prolines [T. E. Michaelson et al. J. Biol. Chem. 252, 883–9 1977], which are thought to provide a flexible joint between the antigen binding and tail domains.

Without wishing to be bound by any theory, the prolines are thought to form the rigid part of the hinge as the ring structure characteristic of this amino acid hinders rotation around the peptide bond that connects the proline residue with an adjacent amino acid. This property is thought to prevent proline, and adjacent residues, from adopting the ordered structure of an alpha helix or beta strand. Flexibility is thought to be imparted by glycine, the simplest amino acid, with very limited steric demands. Glycine is thought to function as a flexible elbow in the hinge. Other amino acids may be substituted for glycine, particularly those without bulky side-chains, such as alanine, serine, asparagine and threonine.

In one preferred embodiment, the hinge region is a chain of four or more amino acids defining the sequence $$—[X]_p—Pro—[Y]_q—Pro—[Z]_r—$$

wherein Pro is proline, X and Y are each glycine, or an amino acid having a non-bulky side chain; Z is any amino acid; p is a positive integer; q is a positive integer of from one to ten; and r is zero or a positive integer greater than zero.

The hinge region can be a discrete region heterologous to both the first and second proteins or can be defined by a carboxy-end portion of the first protein or an amino-end portion of the second protein.

Codons which are infrequently utilised in *E. coli* [H. Grosjean et al, Gene 18, 199–209, 1982] and Salmonella are selected to encode for the hinge, as such rare codons are thought to cause ribosomal pausing during translation of the messanger RNA and allow for the correct folding of polypeptide domains [I. J. Purvis et al. J. Mol. Biol. 193, 413–7 1987]. In addition, where possible restriction enzymes are chosen for the cloning region which, when translated in the resulting fusion, do not encode for bulky or charged side-groups.

In a most preferred aspect, the present invention provides a DNA molecule comprising the nirB promoter operably linked to a DNA sequence encoding first and second polypeptide immunogens linked by a hinge region, wherein the first polypeptide immunogen comprises tetanus toxin fragment C or epitopes thereof.

In another preferred aspect of the invention, there is provided a replicable expression vector, suitable for use in bacteria, containing the nirB promoter sequence operably linked to a DNA sequence encoding first and second polypeptide immunogens linked by a hinge region, wherein the first polypeptide immunogen comprises tetanus toxin fragment C or epitopes thereof.

It has been found that by providing a DNA sequence encoding tetanus toxin fragment C (TetC) linked via a hinge region to a second sequence encoding an antigen, the expression of the sequence in bacterial cells is enhanced relative to constructs wherein the fragment C and hinge region are absent. For example, the expression level of the full length P28 protein of P *S. mansoni* when expressed as a fusion to TetC was greater than when the P28 protein was expressed alone from the nirB promoter. The TetC fusions to the full length P28 protein of *S. mansoni* and its tandem epitopes were all soluble and expressed in both *E. coli* and *S.typhimurium*. In addition, the TetC-P28 fusion protein was capable of being affinity purified by a glutathione agarose matrix, suggesting that the P28 had folded correctly to adopt a conformation still capable of binding to its natural substrate.

Stable expression of the first and second heterologous proteins linked by the hinge region can be obtained in vivo. The heterologous proteins can be expressed in an attenuated bacterium which can thus be used as a vaccine.

The attenuated bacterium may be selected from the genera Salmonella, Bordetella, Vibrio, Haemophilus, Neisseria and Yersinia. Alternatively, the attenuated bacterium may be an attenuated strain of enterotoxigenic *Escherichia coli*. In particular the following species can be mentioned: *S. typhi*—the cause of human typhoid; *S. typhimurium*—the cause of salmonellosis in several animal species; *S. enteritidis*—a cause of food poisoning in humans; *S. choleraesuis*—a cause of salmonellosis in pigs; *Bordetella pertussis*—the cause of whooping cough; *Haemophilus influenzae*—a cause of meningitis; *Neisseria gonorrhoeae*—the cause of gonorrhoea; and Yersinia—a cause of food poisoning.

Attenuation of the bacterium may be attributable to a non-reverting mutation in a gene in the aromatic amino acid biosynthetic pathway of the bacterium. There are at least ten genes involved in the synthesis of chorismate, the branch point compound in the aromatic amino acid biosynthetic pathway. Several of these map at widely differing locations on the bacterial genome, for example aroA (5-enolpyruvylshikimate-3-phosphate synthase), aroC (chorismate synthase), aroD (3-dihydroquinate dehydratase) and aroE (shikimate dehydrogenase). A mutation may therefore occur in the aroA, aroC, aroD, or aroE gene.

Preferably, however, an attenuated bacterium harbours a non-reverting mutation in each of two discrete genes in its aromatic amino acid biosynthetic pathway. Such bacteria are disclosed in EP-A-0322237. Double aro mutants which are suitable are aroA aroC, aroA aroD, and aroA aroE. Other bacteria having mutations in other combinations of the aroA, aroC, aroD and aroE genes are however useful. Particularly preferred are Salmonella double aro mutants, for example double aro mutants of *S. typhi* or *S. typhimurium*, in particular aroA aroC, aroA aroD and aroA aroE mutants. Alternatively, the attenuated bacterium may harbour a non-reverting mutation in a gene concerned with the regulation of one or more other genes (EP-A-0400958). Preferably the mutation occurs in the ompR gene or another gene involved in regulation. There are a large number of other genes which are concerned with regulation and are known to respond to environmental stimuli (Ronson et al, Cell 49, 579–581).

This type of attenuated bacterium may harbour a second mutation in a second gene. Preferably the second gene is a gene encoding for an enzyme involved in an essential biosynthetic pathway, in particular genes involved in the pre-chrorismate pathway involved in the biosynthesis of aromatic compounds. The second mutation is therefore preferably in the aroA, aroC or aroD gene.

Another type of attenuated bacterium is one in which attenuation is brought about by the presence of a non-reverting mutation in DNA of the bacterium which encodes, or which regulates the expression of DNA encoding, a protein that is produced in response to environmental stress. Such bacteria are disclosed in WO 91/15572. The non-reverting mutation may be a deletion, insertion, inversion or substitution. A deletion mutation may be generated using a transposon.

An attenuated bacterium containing a DNA construct according to the invention can be used as a vaccine. Fusion proteins (preferably in substantially pure form) expressed by the bacteria can also be used. in the preparation of vaccines. For example, a purified TetC-P28 fusion protein has been found to be immunogenic on its own. In a further aspect therefore, the invention provides a vaccine composition comprising a pharmaceutically acceptable carrier or diluent and, as active ingredient, an attenuated bacterium or fusion protein as hereinbefore defined.

The vaccine may comprise one or more suitable adjuvants.

The vaccine is advantageously presented in a lyophilised form, for example in a capsular form, for oral administration to a patient. Such capsules may be provided with an enteric coating comprising, for example, Eudragit "S", Eudragit "L", Cellulose acetate, Cellulose acetate phthalate or Hydroxypropylmethyl Cellulose. These capsules may be used as such, or alternatively, the lyophilised material may be reconstituted prior to administration, e.g. as a suspension. Reconstitution is advantageously effected in buffer at a suitable pH to ensure the viability of the organisms. In order to protect the attenuated bacteria and the vaccine from gastric acidity, a sodium bicarbonate preparation is advantageously administered before each administration of the vaccine. Alternatively, the vaccine may be prepared for parenteral administration, intranasal administration or intramammary administration.

The attenuated bacterium containing the DNA construct of the invention may be used in the prophylactic treatment of a host, particularly a human host but also possibly an animal host. An infection caused by a micro-organism, especially a pathogen, may therefore be prevented by administering an effective dose of an attenuated bacterium according to the invention. The bacterium then expresses a heterologous protein or proteins capable of raising antibody to the micro-organism. The dosage employed will be dependent on various factors including the size and weight of the host, the type of vaccine formulated and the nature of the heterologous protein.

An attenuated bacterium according to the present invention may be prepared by transforming an attenuated bacterium with a DNA construct as hereinbefore defined. Any suitable transformation technique may be employed, such as electroporation. In this way, an attenuated bacterium capable of expressing a protein or proteins heterologous to the bacterium may be obtained. A culture of the attenuated bacterium may be grown under aerobic conditions. A sufficient amount of the bacterium is thus prepared for formulation as a vaccine, with minimal expression of the heterologous protein occurring.

The DNA construct may be a replicable expression vector comprising the nirB promoter operably linked to a DNA sequence encoding the tetanus toxin C fragment or epitopes thereof and the second heterologous protein, linked by a hinge region. The nirB promoter may be inserted in an expression vector, which already incorporates a gene encoding one of the heterologous proteins (e.g. tetanus toxin C fragment), in place of the existing promoter controlling expression of the protein. The hinge region and gene encoding the second heterologous protein (e.g. an antigenic sequence) may then be inserted. The expression vector should, of course, be compatible with the attenuated bacterium into which the vector is to be inserted.

The expression vector is provided with appropriate transcriptional and translational control elements including, besides the nirB promoter, a transcriptional termination site and translational start and stop codons. An appropriate ribosome binding site is provided. The vector typically comprises an origin of replication and, if desired, a selectable marker gene such as an antibiotic resistance gene. The vector may be a plasmid.

The invention will now be illustrated but not limited, by reference to the following examples and the accompanying drawings, in which.

Figure 2:
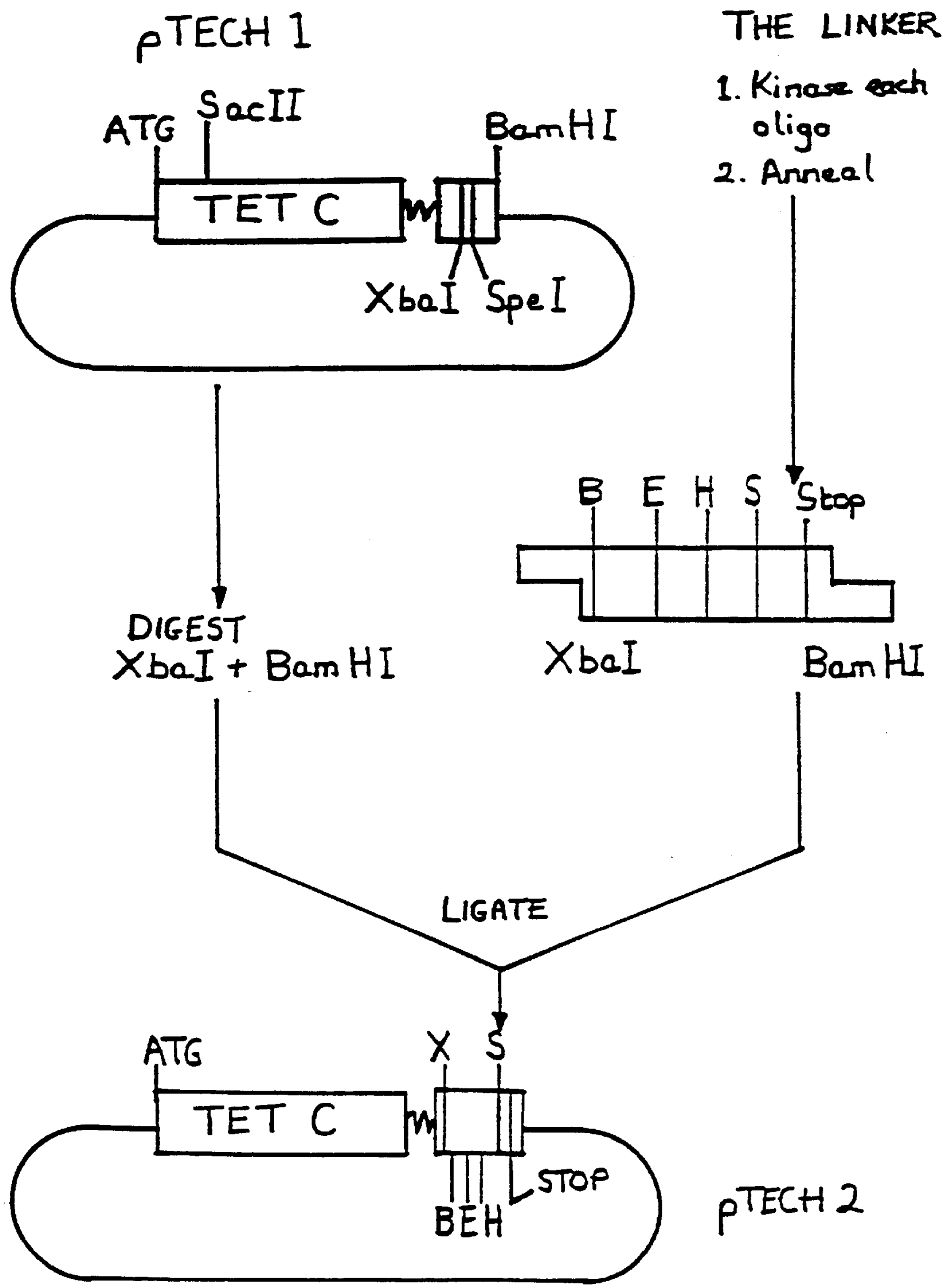
FIG. 2 is a schematic illustration of the construction of a second intermediate plasmid pTECH2.
Figure 3:
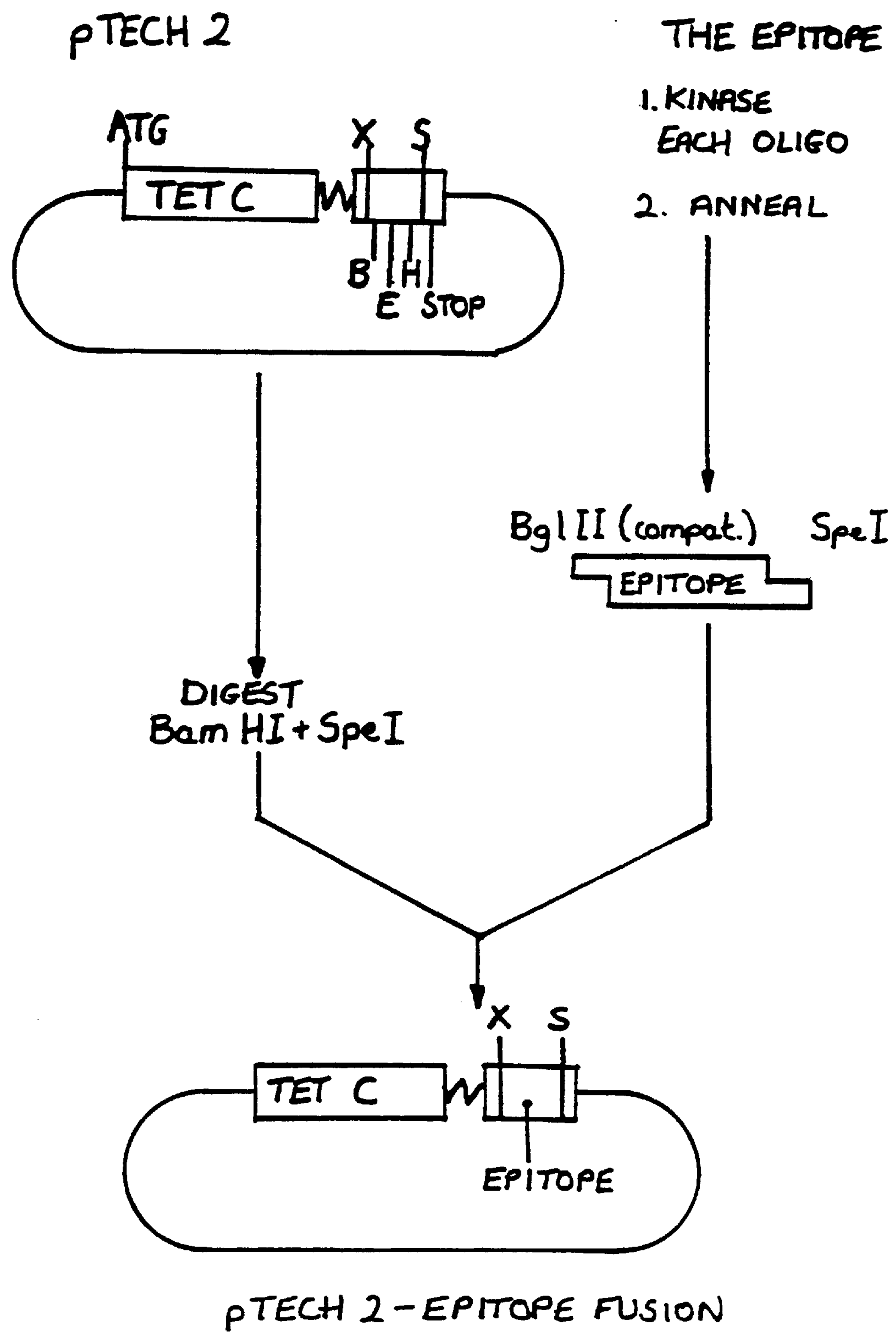

FIG. 3 is a schematic illustration of the construction of a plasmid of the invention using the intermediate plasmid of FIG. 2 as the starting material. In FIG. 3 B=BamHI, E=EcoRV; H=HindIII; X=XbaI; S=apeI.

Figure 4:
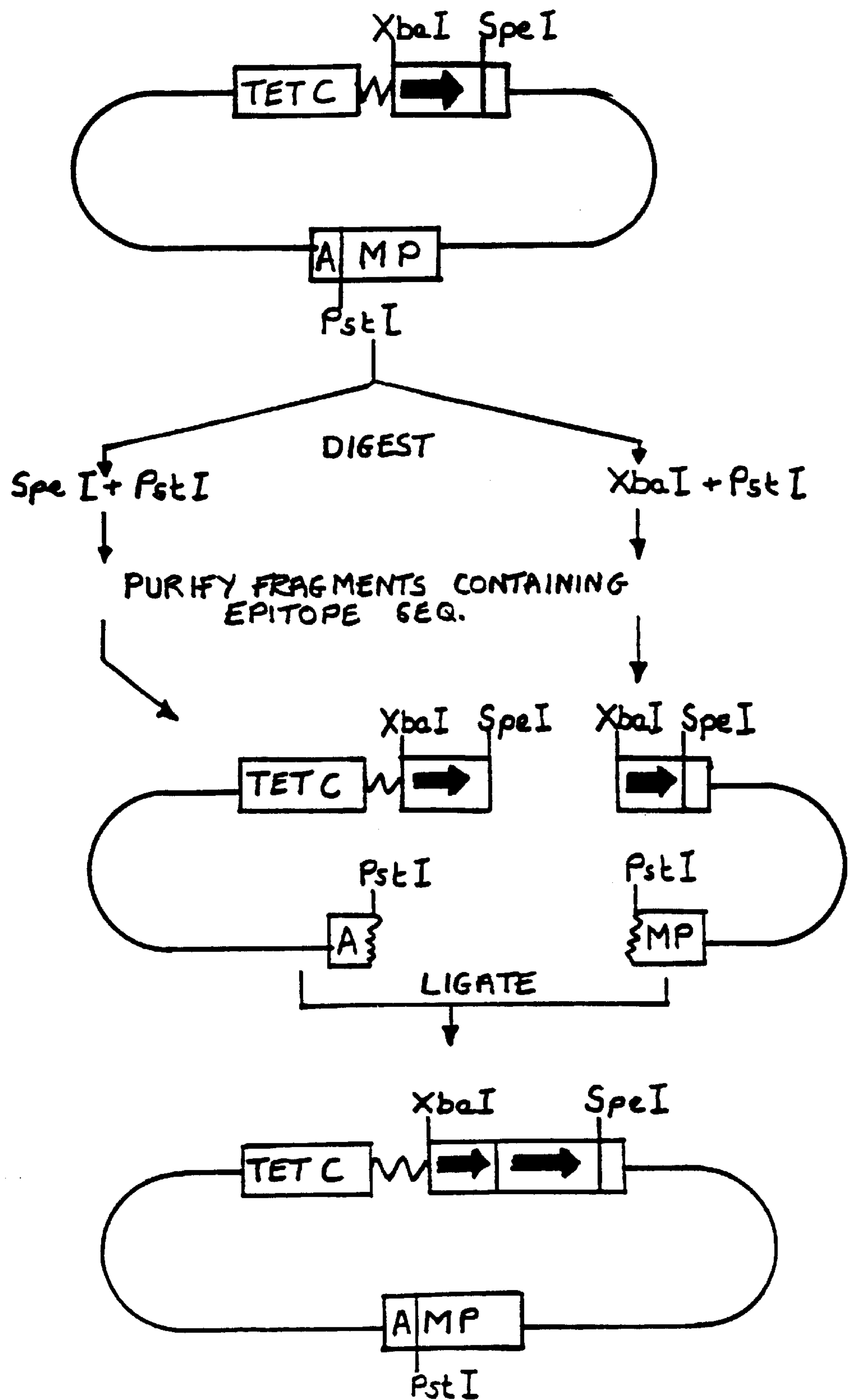

FIG. 4 is a schematic illustration of the construction of a plasmid containing repeating epitopes (repitopes).

FIG. 5 illustrates antibody responses against recombinant *S. mansoni* protein P28 as detected by ELISA in mice inoculated intravenously with (FIG. 5A) SL3261, (FIG. 5B) SL3261 (pTETnir15), (FIG. 5C) SL3261 (pTECH2), (FIG. 5D) SL3261 (pTECH2-monomer), (FIG. 5E) SL3261 (pTECH2-dimer), (FIG. 5F) SL3261 (pTECH2-tetramer), (FIG. 5G) SL3261 (pTECH2-octamer), and (FIG. 5H) SL3261 (pTECH1-P28). In FIG. 5, the results are expressed as OD in individual mice at intervals after immunization.

Figure 6:
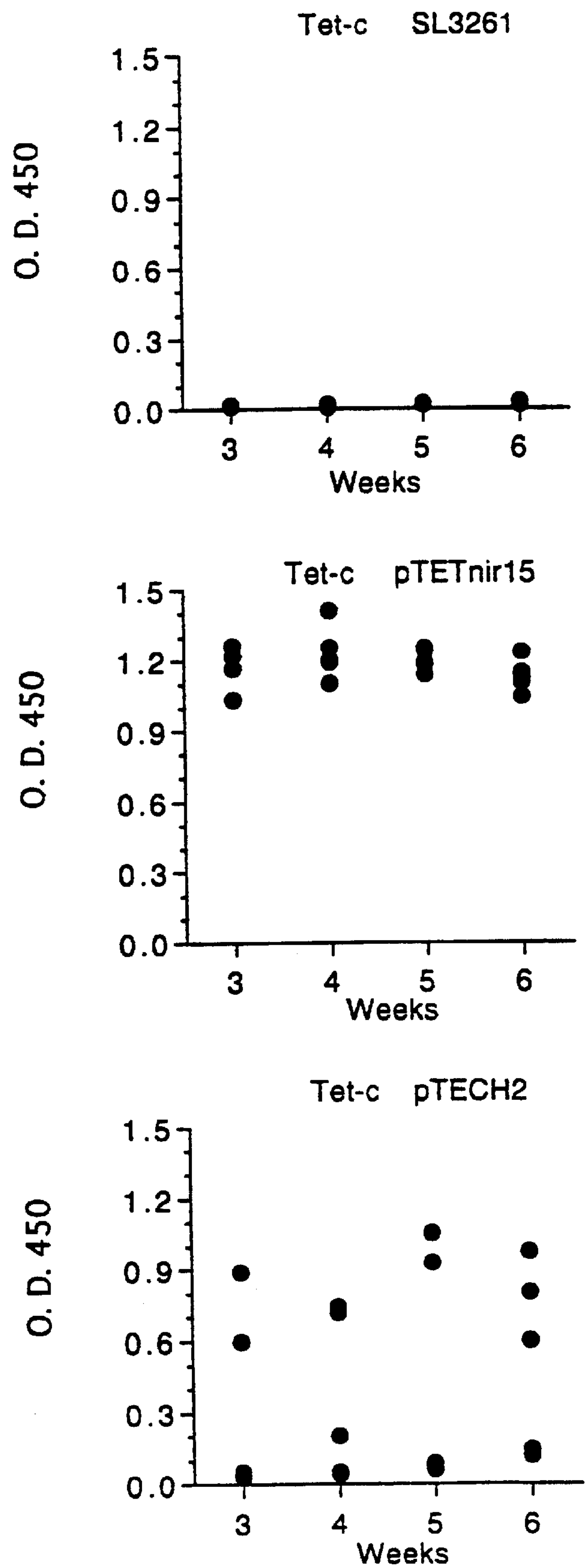

FIG. 6 illustrates antibody responses against TetC as detected by ELISA in mice inoculated as in FIG. 5: (FIG. 6A) SL3261, (FIG. 6B) SL3261 (pTETnirl5), (FIG. 6C) SL3261 (pTECH2), (FIG. 6D) SL3261 (pTECH2-moncomer), (FIG. 6E) SL3261 (pTECH2-dimer), (FIG. 6F) SL3261 (pTECH2-tetramer), (FIG. 6G) SL3261 (pTECH2-octamer), and (FIG. 6H) SL3261 (pTECH1-P28).

Figure 7:
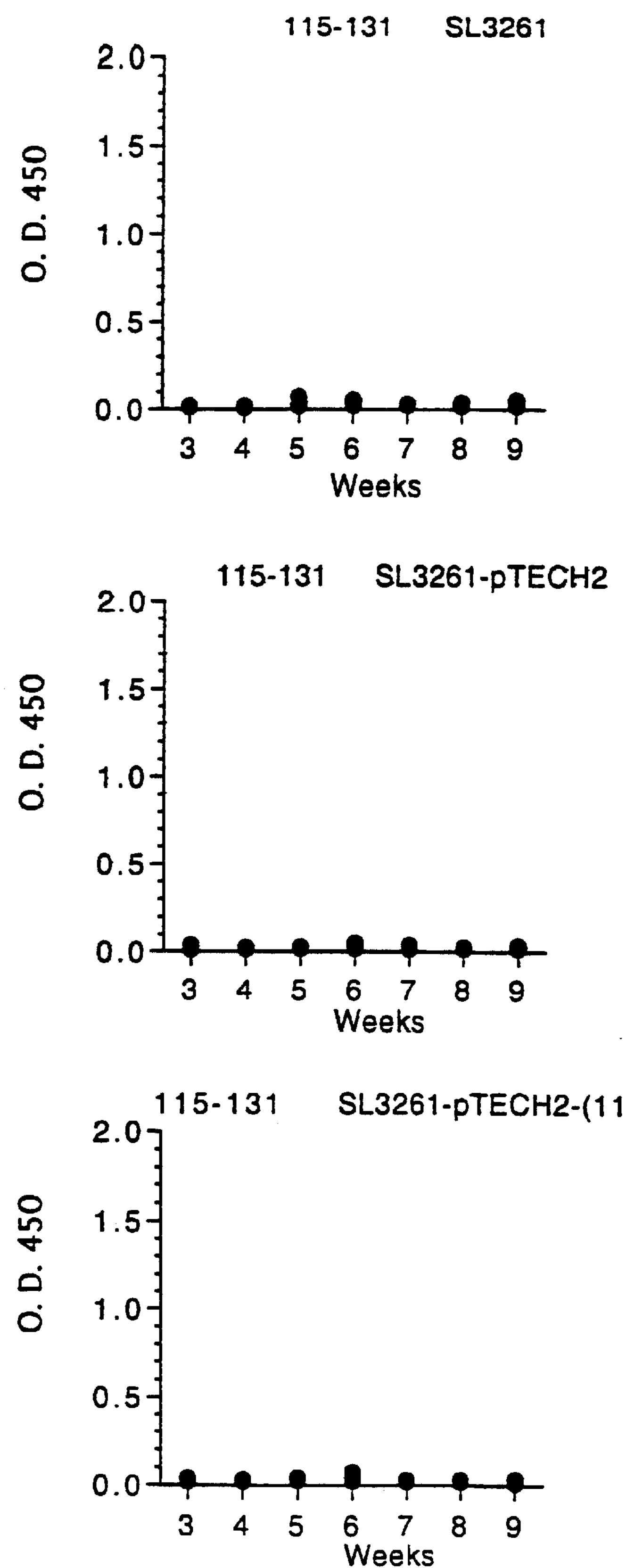
Figure 7:
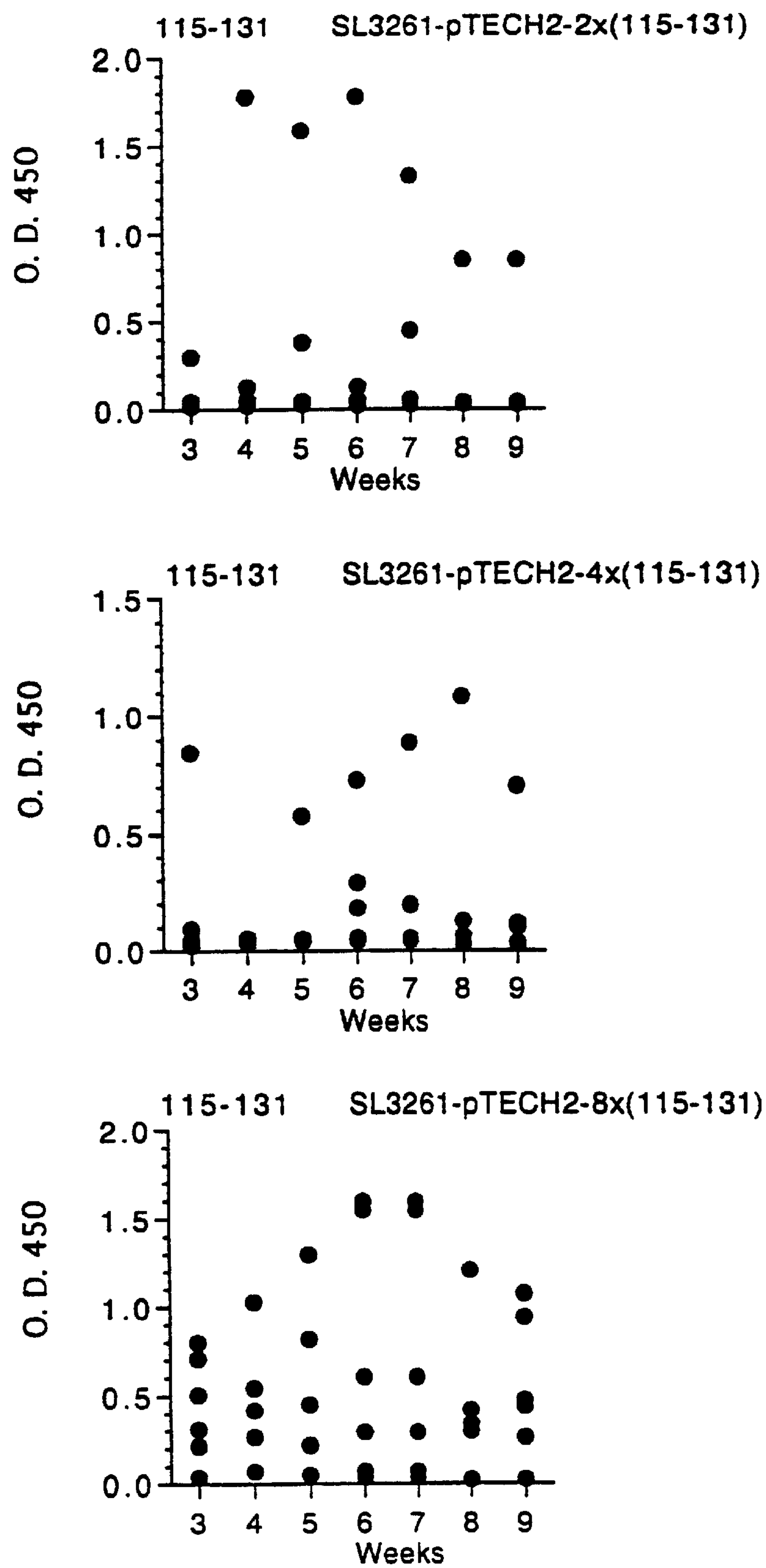

FIG. 7 illustrates antibody responses against peptide 115–131 of the P28 protein coupled to ovalbumin as detected by ELISA in mice inoculated intravenously with (FIG. 7A) SL3261, (FIG. 7B) SL3261 (pTECH2), (FIG. 7C) SL3261 (pTECH2-monomer), (FIG. 7D) SL3261 (pTECH2-dimer), (FIG. 7E) SL3261 (pTECH2-tetramer), and (FIG. 7F) SL3261 (pTECH2-octainer).

Figure 8:
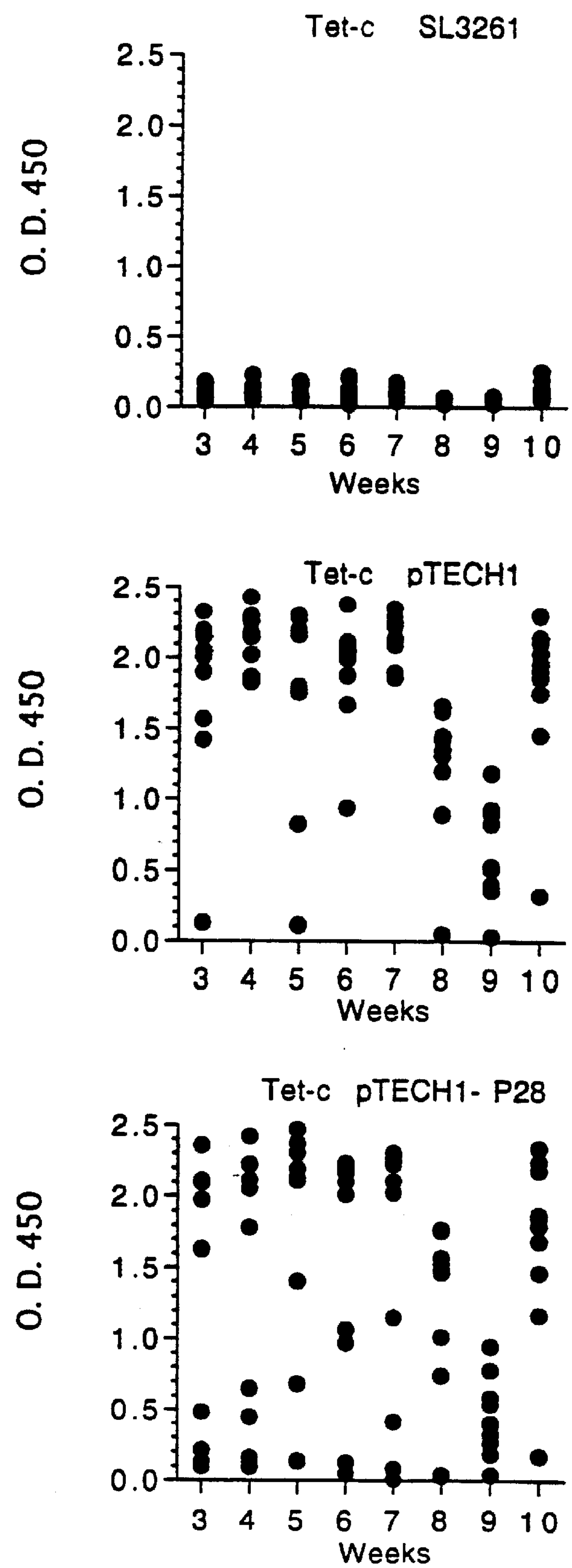

FIG. 8 illustrates antibody responses against TetC as detected by ELISA from mice inoculated orally with SL3261 (pTECH1-P28): (FIG. 8A) SL3261, (FIG. 8B) SL3261 (pTECH1), (FIG. 8C) SL3261 (pTECH1-P28).

Figure 9:
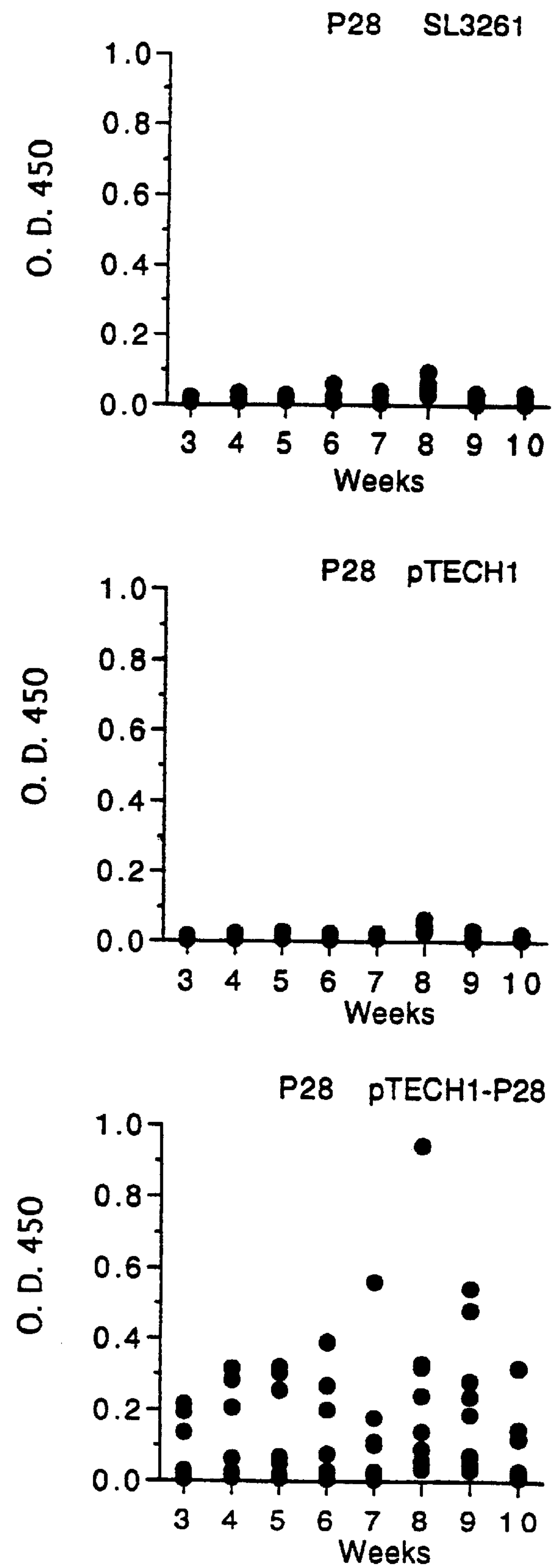

FIG. 9 illustrates antibody responses against recombinant P28 as detected by ELISA in mice inculated as in FIG. 8: (FIG. 9A) SL3261, (FIG. 9B) SL3261 (pTECH1), (FIG. 9C) SL3261 (pTECH1 -P28).

Figure 10:
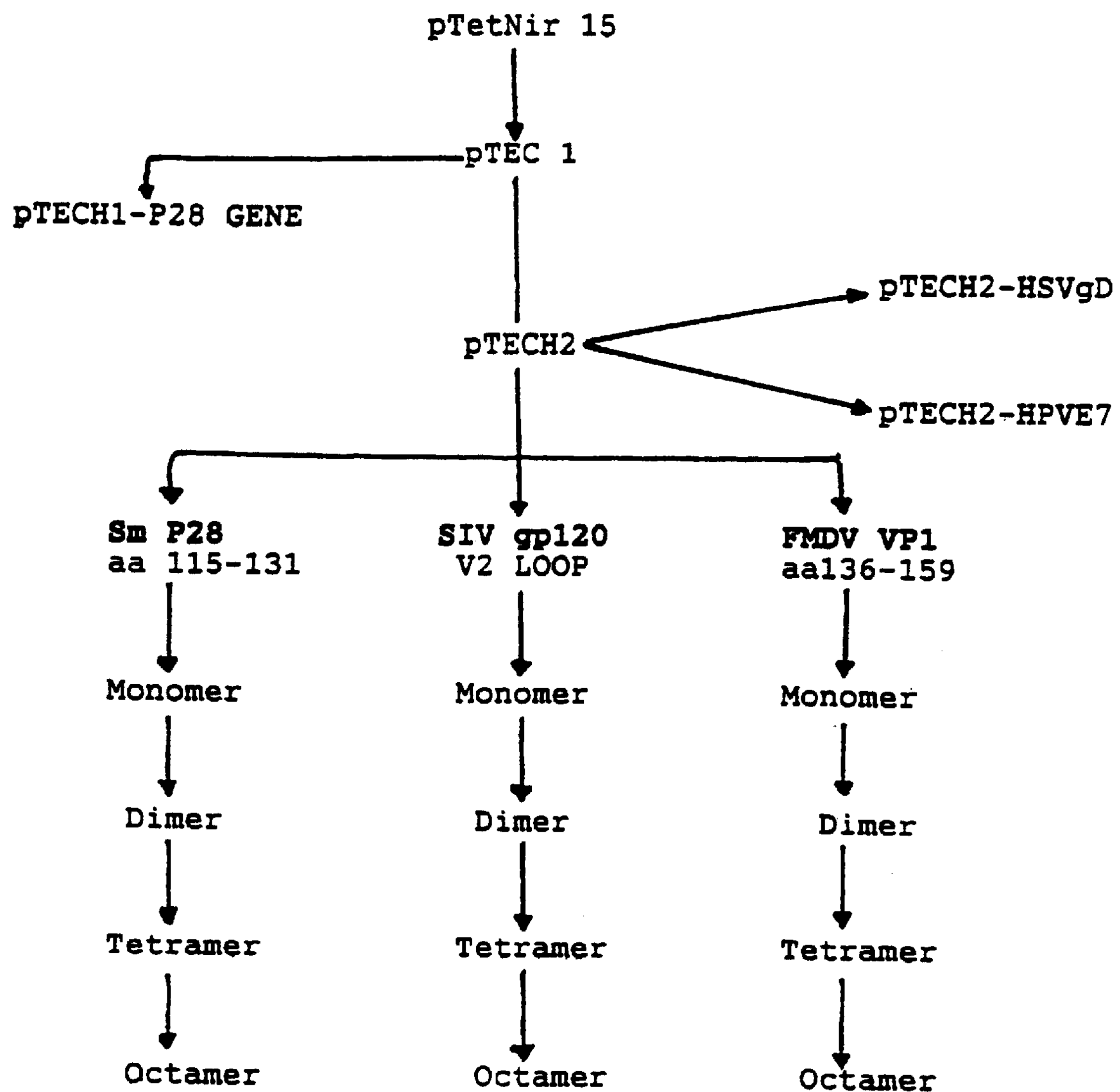

FIG. 10 illustrates schematically the preparation of various constructs from the pTECH2 intermediate plasmid.

Figure 11:
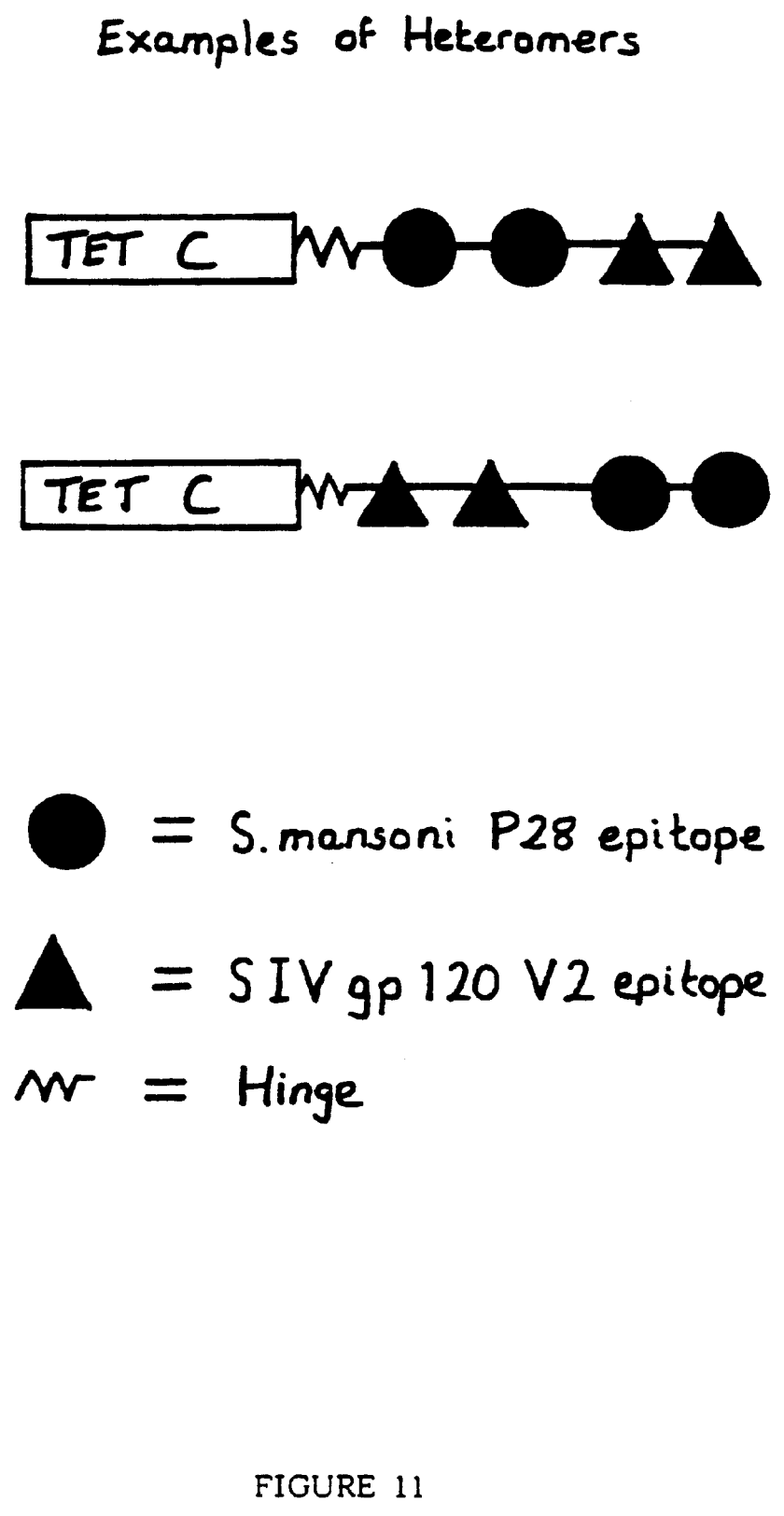

FIG. 11 illustrates schematically the structure of tripartite protein structures (“heteromers”) prepared using pTECH2.

FIG. 12 shows the DNA sequence of the vector pTECH1. (SEQ ID NO: 17).

FIG. 13 shows the DNA sequence of the vector pTECH2. (SEQ ID NO: 18).

Figure 14:
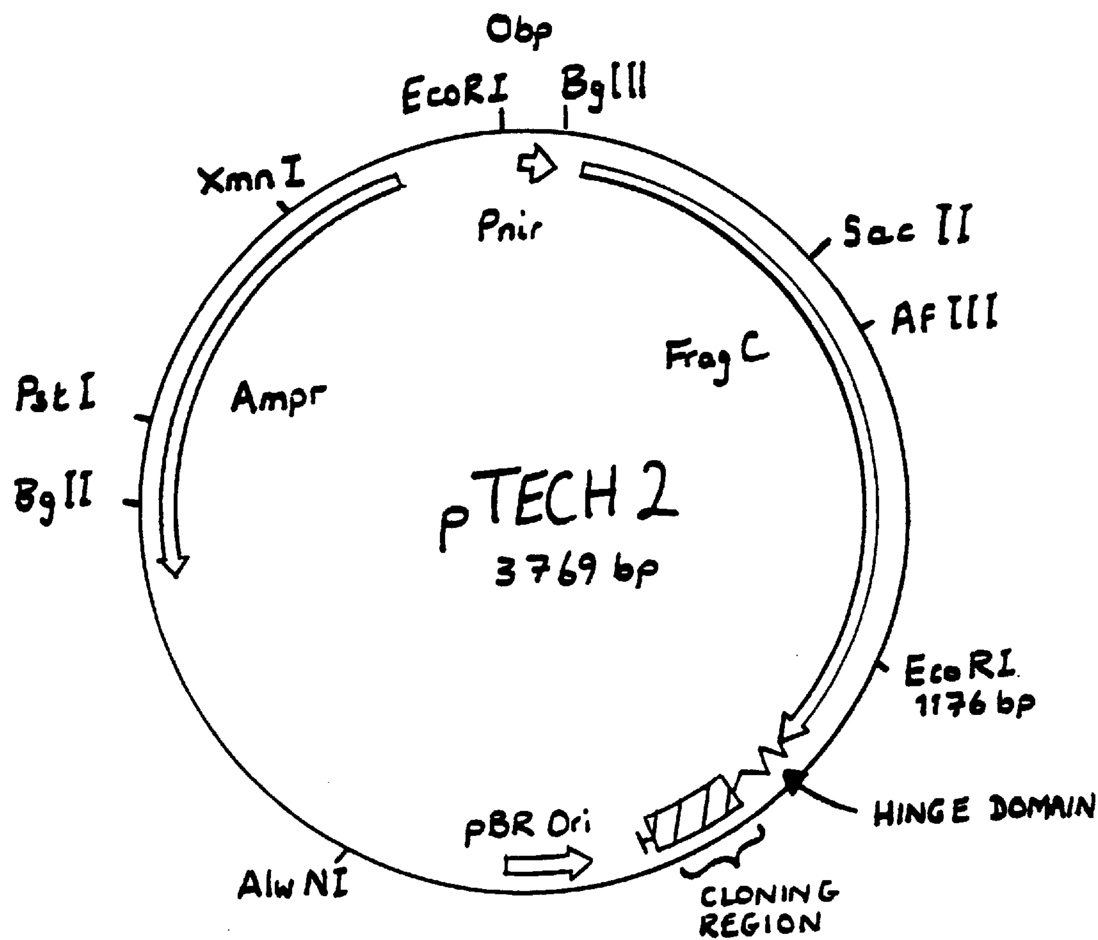

FIG. 14 illustrates, schematically, the restriction sites on the vector pTECH2.

EXAMPLE 1

PreDaration of pTECH1

Figure 1:
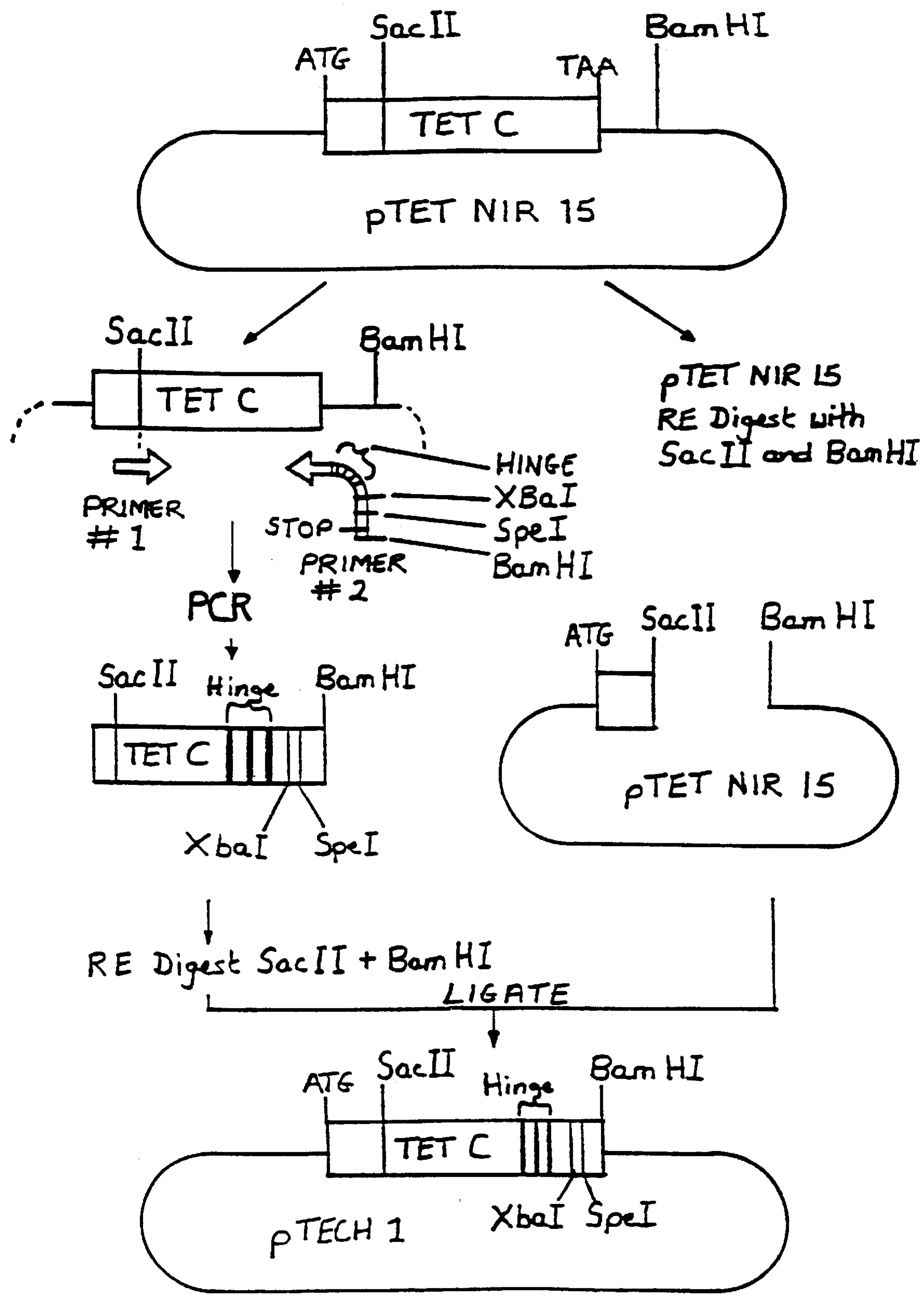
FIG. 1 is a schematic illustration of the construction of an intermediate plasmid pTECH1 in accordance with one aspect of the invention.

The preparation of pTECH1, a plasmid incorporating the nirB promoter and TetC gene, and a DNA sequence encoding a hinge region and containing restriction endonuclease sites to allow insertion of a gene coding for a second or guest protein, is illustrated in FIG. 1. Expression plasmid pTETnir15, the starting material shown in FIG. 1, was constructed from pTETtac115 (Makoff et al, Nucl. Acids Res. 17 10191–10202, 1989); by replacing the EcoRI-ApaI region (1354bp) containing the lacI gene and tac promoter with the following pair of oligos 1 and 2: Oligo-1 5'AATTCAGGTAAATTTGATGTACATCAAATGGTACCCCTTGCTGAAT Oligo-2 3'-GTCCATTTAAACTACATGTAGTTTACCATGGGGAACGACTTA CGTTAAGGTAGGCGGTAGGGCC-3' (SEQ ID NO: 2) GCAATTCCATCCGCCATC-5' (SEQ ID NO: 3)

The oligonucleotides were synthesised on a Pharmacia Gene Assembler and the resulting plasmids confirmed by sequencing (Makoff et al, Bio/Technology 7, 1043–1046, 1989). The pTETnir15 plasmid was then used for construction of the novel pTECH1 plasmid incorporating a polylinker region suitable as a site for insertion of heterologous DNA to direct the expression of fragment C fusion proteins. pTETnir15 is a known pAT153-based plasmid which directs the expression of fragment C. However, there are no naturally occurring convenient restriction sites present at the 3'-end of the TetC gene. Therefore, target sites, preceded by a hinge region, were introduced at the 3'-end of the TetC coding region by means of primers tailored with “add-on” adapter sequences (Table 1), using the polymerase chain reaction (PCR) [K. Mullis et al, Cold Spring Harbor Sym. Quant. Biol. 51, 263–273 1986]. Accordingly, pTETnir15 was used as a template in a PCR reaction using primers corresponding to regions covering the SacII and BamHI sites. The anti-sense primer in this amplification was tailored with a 38 base 5'-adaptor sequence. The anti-sense primer was designed so that a sequence encoding novel XbaI, SpeI and BamHI sites were incorporated into the PCR product. In addition, DNA sequences encoding additional extra amino acids including proline were incorporated (the hinge regions) and a translation stop codon signal in frame with the fragment C open reading frame.

The PCR product was gel-purified and digested with SacII and BamHI, and cloned into the residual 2.8 kb vector pTETnir15 which had previously been digested by SacII and BamHI. The resulting plasmid purified from transformed colonies and named pTECH 1 is shown in FIG. 1. Heterologous sequences such as the sequence encoding the *Schistosoma mansoni* P28 glutathione S-transferase (P28) were cloned into the XbaI SpeI and BamHI sites in accordance with known methods.

EXAMPLE 2

Construction of pTECH2

To further improve the utility of pTECH1, a short linker sequence was introduced between the XbaI and BamHI sites in pTECH1 to allow the directional cloning of oligonucleotides and to also facilitate the construction of multiple tandem epitopes, (“repitopes”) (FIG. 2). Two complementary oligonucleotides were synthesised bearing the restriction enzyme target sites for BamHI, EcoRV, HindIII, SpeI, followed by a translational stop codon (Table 1). The oligonucleotides were tailored with XbaI and BamHI cohesive ends; however, the BamHI target sequence was designed to include a mismatch and, upon cloning, this restriction site in pTECH1 is destroyed. This version of the vector was designated pTECH2.

EXAMPLE 3

Construction of PTECH1-P28

A P28 gene expression cassette was produced by PCR using pUC19-P28 DNA (a kind gift from Dr R Pierce, Pasteur Institute, Lille) as template. Oligonucleotide primers were designed to amplify the full length P28 gene beginning with the start codon and terminating with the stop codon. In addition, the sense and antisense primers were tailored with the restriction sites for XbaI and BamHI respectively. The product was gel-purified and digested with XbaI and BamHI and then cloned into pTECH1 which had previously been digested with these enzymes and subsequently gel-purified.

Expression of the TetC-P28 Fusion Protein

Expression of the TetC-P28 fusion protein was evaluated by SDS-PAGE and Western blotting of bacterial cells harbouring the construct It was found that the fusion protein remains soluble, cross-reacts with antisera to both TetC and P28, and is also of the expected molecular weight, 80 kDal, for a full length fusion.

The fusion protein was stably expressed in a number of different genetic backgrounds including *E. coli* (TG2) and *S. typhimurium* (SLB338,SL3261) as judged by SDS-PAGE and Western blotting. Of interest was a minor band of 50 kDal which co-migrates with the TetC-Hinge protein alone and cross-reacts exclusively with the anti-TetC sera is visible in a Western blot. As the codon selection in the hinge region has been designed to be suboptimal, the rare codons may cause pauses during translation which may occasionally lead to the premature termination of translation, thus accounting for this band.

Affinity Purification of the TetC-P28 Fusion

Glutathione is the natural substrate for P28, a glutathione S-transferase. The amino acid residues involved in binding glutathione are thought to be spatially separated in the primary structure of the polypeptide and brought together to form a glutathione binding pocket in the tertiary structure (P. Reinemer et al. EMBO, J8, 1997–2005, 1991). In order to gauge whether the P28 component of the fusion has folded correctly to adopt a conformation capable of binding glutathione, its ability to be affinity purified on a glutathione-agarose matrix was tested. The results obtained (not shown) demonstrated that TetC-P28 can indeed bind to the matrix and the binding is reversible, as the fusion can be competitively eluted with free glutathione.

EXAMPLE 4

Construction of pTECH2-P28(aa115–131) Peptide Fusions

Complementary oligonucleotides encoding the aa115–131 peptide were designed with a codon selection for optimal expression in *E. coli* [H. Grosjean et al idem]. The oligonucleotides were tailored with BglII and SpeI cohesive ends which were generated upon annealing and cloned into pTECH2 which had previously been digested with BamHI and SpeI (FIG. 3).

Repeated tandem copies of the epitopes (repitopes) were constructed in pTECH2 by the following approach. The recombinant fusion vector was digested with XbaI and SpeI and to each digest was added a second restriction enzyme which cuts uniquely elsewhere within the vector, e.g. PstI which makes a cut exclusively within the ampicillin resistance gene (FIG. 4). DNA fragments containing the epitope sequences can be purified from each of the double digests, mixed and then ligated. XbaI cleaves its target sequence to generate a 5'-CTAG overhang which is compatible with the SpeI overhang. Upon ligation the recognition sequences of both these enzymes are destroyed. In this way the XbaI-SpeI restriction sites remain unique and the procedure can be simply and effectively repeated to construct recombinant fusion vectors expressing four or eight tandem copies of the epitopes (FIG. 4). A similar strategy has been used by others in the generation of a multimeric fusion protein for the production of a neuropeptide [T. Kempe et al. Gene 39, 239–45, 1985].

Expression of the TetC-peptide Fusion proteins

Expression of the TetC-peptide fusions as monomeric, dimeric, tetrameric, and octameric tandem peptide repeats was evaluated by SDS-PAGE and Western blotting of the bacterial strains harbouring the constructs. The fusion proteins remain soluble, cross-react with both antisera to TetC and P28, and are also of the expected molecular weight [FIG. 5]. Furthermore the fusion proteins are expressed in a number of different genetic backgrounds including *E. coli* (TG2) and *S. typhimurium* (SL5338, SL3261) as judged by SDS-PAGE and Western blotting. There appeared to be some degradation of the repitopes consisting of higher numbers of copies, as indicated by the appearance of faint bands of lower molecular weight seen in Western blots probed with the anti-P28 antibody.

The size of the bands suggested that they consisted of reduced copy number fusions to TetC. As was the case with the TetC-P28 fusion described above, the level of expression of the TetC-peptide fusions was less than that of TetC alone from pTECH2, with the expression level gradually decreasing with increasing copy number.

EXAMPLE 5

Immunological Studies

Stability of the Plasmid Constructs in vivo and Immunisation of Mice

BALB/c mice were given approx. $10^6$ cfu i/v or $5\times10^9$ orally of *S. tyohimurium* SL3261 and SL3261 harbouring the different constructs. Viable counts on homogenates of liver, spleen and (for orally inoculated mice) lymph nodes performed from days 1–8 (epitope fusions) and 1–11 (vector, octamer and P28 fusions) were similar on media with and without ampicillin, indicating that the plasmids were not being lost during growth in the tissues.

Antibody Responses in Mice Immunised Intravenously

Antibody Responses to the TetC-P28 Fusion

Tail bleeds were taken weekly on weeks 3 to 6 from animals from each group of 8 mice. FIG. 5 shows that in mice immunised with salmonellae expressing the TetC-P28 fusion, antibody responses to recombinant P28 appeared by week 3, and were positive in 6/6 mice from week 4 onwards. No anti-P28 antibodies were detected in sera from mice immunised with either SL3261 or SL3261-pTETnir15 or pTECH2.

All mice immunised with salmonellae expressing TetC, either alone or as the TetC-P28 fusion (but not with salmonellae alone), made antibody to TetC appearing as early as the third week. (FIG. 6).

Antibody Responses to the TetC-peptide Fusions

Mice immunised with salmonellae expressing TetC fused to multiple copies of the aa 115–131 peptide were bled as above and the sera tested by ELISA against the synthetic 115–131 peptide chemically conjugated to ovalbumin, and against recombinant P28. FIG. 7 shows that antibody responses to the peptide were detected as early as week 3 and increased thereafter, with responses being stronger to fusions containing greater numbers of copies of the peptide. The octameric fusions elicited the best responses with 4–5 mice positive. No antibody responses were detected against ovalbumin-monomer or recombinant P28 in mice immunised either with SL3261, pTECH2 or the monomeric epitope fusion.

Some of the anti-epitope sera recognised the full length P28 protein in ELISA (FIG. 5). One mouse injected with the dimeric fusion was positive at week 5, another mouse injected with the tetrameric fusion was positive at week 3. Thereafter sera from at least two mice injected with the octameric fusion consistently recognised P28 from week four up to week six.

In summary the antibody responses against the repitopes improved dramatically with increasing copy number, with the tetrameric and octameric repitope fusions being the most potent. No antibody responses to the monomeric fusion were detected.

Antibody Response to TetC in Mice Immunised with the Different Fusions

The antibody response to TetC was not the same in all groups; the addition of C-terminal fusions to TetC clearly modified the response. FIG. 6 shows that the antibody response to TetC elicited by the vector pTECH2 (TetC-Hinge alone) was significantly less than the TetC response to the parental vector, pTETnir15. Surprisingly, the addition to TetC of fusions of increasing size dramatically restores the response to TetC. The anti-TetC response to the largest fusion, full length P28 in pTECH1, was similar to the response to TetC obtained from the parental plasmid (under the conditions tested). Sera from mice injected with non-recombinant SL3261 did not react with TetC at any time during the period tested.

Antibody Responses in Mice Immunised Orally

Groups of 10 mice were immunised orally with approx. $5\times10^9$ cfu of SL3261 alone or carrying pTECH1, or pTECH1-P28, given intragastrically in 0.2 ml via a gavage tube. Bleeds taken from week 3 to week 10 showed that most mice receiving the recombinant salmonellae made antibody to TetC as early as week 3 (FIG. 8). Mice immunised with the TetC-P28 fusion made antibody to P28 which was detectable in approximately half of the mice by week 8, and then declined (FIG. 9).

Antibody Responses in Mice Immunised with the Purified Fusion Protein

Mice were immunised subcutaneously with affinity purified TetC-P28 fusion protein adsorbed on aluminium hydroxide. Controls received commercial tetanus toxoid alone. Preliminary results indicate that animals given the fusion protein make an antibody response to both TetC and to P28 (data not shown). No anti-P28 antibody was detected in mice given tetanus toxoid.

T-cell Responses to TetC and P28

Mice were immunised i/v with approximately $10^6$ cfu of SL3261, SL3261(pTETnir15) and SL3261(pTECH1-P28). Six months later T-cell responses as IL-2/IL-4 production were measured against salmonella whole cell soluble extract, TetC, recombinant P28 and whole adult worm antigen as described in the section headed Materials and Methods below. Table 2 shows that cells from both groups produced an IL-2/IL-4 response to the sodium hydroxide treated salmonella extract and to TetC. However, cells from mice immunised with the salmonellae expressing the TetC-P28 fusion also responded to both recombinant P28 and whole worm extract.

Thus the salmonella delivery system has elicited both humoral and cellular (T-cell) immune responses to P28.

The salmonellae expressing the recombinant antigens all persisted in the mouse tissues as well as the parental strain, and the plasmids were not lost in vivo.

Constructs expressing higher molecular weight fusions (full length P28 and octamer) proved to be the most immunogenic. It may be that the immune response has been promoted by the carrier TetC providing additional T-cell helper epitopes [Francis et al. Nature 330: 168–170, 1987]. By week 4 all the mice immunised with cells carrying pTECH1-P28 responded to both TetC and also the full length P28 protein following i/v immunisation. Mice immunised orally also responded to TetC and P28, although not all the mice responded to P28. It may well be that the response to P28, could be improved by boosting. Improved constructs consisting of codon optimised hinge regions, codon optimised P28, and multiple copies of full length P28, are currently in preparation.

The antibody responses to the epitopes improved dramatically with increasing copy number, with the tetramer and octamer "repitope" fusions displaying the greatest potency.

EXAMPLE 6

Cloning of HPVE7 Protein in pTECH2

The full-length HPV type 16 E7 protein gene was cloned into plasmid pTECH2 by an in frame insertion of the gene in the BamHI site of the vector hinge region.

The E7 gene was obtained from plasmid pGEX16E7 (S. A. Comerford et al. J Virology, 65, 4681–90 1991). The gene in this plasmid is flanked by two restriction sites: a 3' BamHI site and a 5' EcoRI site. pGEX16E7 DNA was digested with EcoRI and blunt ended by a filling up reaction using Sequenase (DNA polymerase from USB). It was then digested with BamHI to release the 0.3 Kbp full length E7 gene.

The gel purified gene was ligated to BamHI-EcoRV double digested pTECH2 and this ligation mixture used to transform competent *E. coli* HB101 bacteria.

Recombinant colonies were selected by colony blotting using two monoclonal antibodies against HPV16 E7 protein as probes, namely 6D and 4F (R. W. Tindle, et al J Gen. Vir. 71,1347–54 1990). One of these colonies, named pTE79, was chosen for further analysis.

Protein extracts from pTE79 transformed *E. coli* grown in both aerobic and anaerobic conditions were prepared and analysed by SDS-PAGE and Western blotting. Growth in anaerobic conditions resulted in expression of a recombinant molecule of about 60 KDal which reacted with monoclonal antibodies 6D and 4F and a rabbit polyclonal serum against Tetanus fragment C.

EXAMPLE 7

Construction of PTECH2-gD

An immunologically important antigen from herpes simplex virus type 1 [HSV1] is glycoprotein D, termed gD1 (R.

J. Watson et al Science 218, 381–383 1982). A truncated gD1 gene cassette, lacking the transmembrane and cytoplasmic domains aa26–340, was synthesised by PCR. The PCR primers used are shown in Table 3. The forward primer was designed to encode the N-terminus of the mature protein and the reverse primer encoded the amino acids immediately 5' to the transmembrane domain. In addition the primers were tailored with BamHI and SpeI restriction sites respectively. The template for the PCR reation was the plasmid pRWFG [a HSV1 gD BamHI-J clone from strain Patton in pBR322; a kind gift from Dr. T. Minson, Cambridge University]. The amplification product was digested with BamHI and SpeI and cloned into pTECH2 which had previously been digested with the respective enzymes.

Expression of the TetC-gD1 fusion protein was assessed by SDS-PAGE and Western blotting of bacterial strains harbouring the constructs. The Western blots were probed with either anti-TetC polyclonal sera or a monoclonal anitbody directed against amino acids 11–19 of the mature gD [designated LP16, obtained from Dr. T. Minson, Cambridge]. The fusion protein is expressed as a 85 kDal band visible on Western blots together with lower molecular weight bands down to 50 kDal in size. The lower molecular weight bands could correspond to proteolytic cleavage products of gD or represent the products of premature translational termination within the coding region of gD due to ribosomal pausing. The fusion protein is expressed in the salmonella strains SL5338 and SL3261.

EXAMPLE 8

Construction of PTECH2—FMDV/SIV Repitopes

Peptides from the foot and mouth disease virus (FMDV; serotype A12] viral proteinl [VP1; aal36–159] and the V2 loop from simian immunodeficiency virus [SIV] envelope protein [gp120; aa171–190] were cloned into pTECH2 (M. P. Broekhuijsen et al J. Gen. Virol. 68, 3137–45 1987; K. A. Kent et al. AIDS Res. and Human Retro. 8:1147–1151 1992].

Complementary oligonucleotides encoding the peptides were designed with a codon selection for optimal expression in *E. coli* [H. Grosjean et al Gene, 18, 199–209, 1982]. The oligonucleotides are shown in Table 3. The oligonucleotides were tailored with BqlII and SpeI cohesive ends which were generated upon annealing and cloned into pTECH2 which had previously been digested with BamHI and SpeI (FIG. 3). Dimeric, tetrameric and octameric fusions of these peptides were constructed as described previously.

Expression of the TetC-fusions was assessed by SDS-PAGE and Western blotting with a polyclonal sera directed against TetC and monoclonal antibodies directed against either the FMDV or the SIV epitopes. The FMDV and SIV repitope constructs expressed the TetC fusion proteins in both SL5338 and SL3261.

EXAMPLE 9

Construction of pTECH2—gp120-P28 Peptide Heteromers

To explore the possibility of delivering more than one type of epitope from a single molecule of TetC, fusions have been made with the P28 and SIV repitopes to produce a tripartite protein. This form of construction has been facilitated by the modular nature of the vector which allows the assembly of vector modules containing different repitopes. These "heteromers" express either tandem dimers or tetramers of the P28 and SIV repitopes. To investigate the effect of the position of a particular repitope in the TetC-Repitope A-Repitope B fusion on its expression level, stability, and immunogenicity, the converse combinations have also been constructed i.e. TetC-Repitope B-Repitope A, as is shown in FIG. 11. "Heteromers" constructed in this way are TetC-P28 dimer-SIV dimer, TetC-SIV dimer-P28 dimer, TetC-P28 tetramer-SIV tetramer and TetC-SIV tetramer-P28 tetramer.

Expression of the tripartite fusions were evaluated by SDS-PAGE and Western blotting using the antibody reagents described above. These heteromer constructs are all expressed in the Salmonella strains SL5338 and SL3261, but intriguingly the expression level and stability is greater in one dimer-dimer and tetramer-tetramer combination (TetC-gp120-P28] than the converse.

EXAMPLE 10

MATERIALS AND METHODS

Plasmids, Oligonucleotides, and the Polymerase Chain Reaction

The plasmid pTETnir15 directs the expression of fragment C from tetanus toxin under the control of the nirB promoter [Chatfield et al. idem Oxer et al. idem The TetC-hinge fusion vector pTECH1 was constructed from pTETnir15 by the polymerase chain reaction (PCR) described by Mullis et al, 1986. PCR was performed using the high-fidelity thermostable DNA polymerase from *Pyrococcus furiosus*, which possesses an associated 3'-5' exonuclease proofreading activity [K. S. Lundberg et al Gene 108: 1–6, 1991]. The amplification reaction was performed according to the manufacturer's instructions (Stratagene).

Bacterial Strains

The bacterial strains used were *E. coli* TG2 (recA; [J. Sambrook et al. Molecular cloning: a laboratory manual. Cold Spring Harbor, N.Y., 1989]). *S. typhimurium* SL5338 (galE $r^-m^+$ [A. Brown J. Infect. Dis. 155: 86–92, et al J. Infect. Dis. 155: 86–92, 1987]) and SL3261 (aroA); [S. K. Hoiseth et al Nature 291, 238–9, 1981]. Bacteria were cultured in either L or YT broth and on L-agar with ampicillin (50 μg/ml) if appropriate. Plasmid DNA prepared in *E. coli* was first modified by transformation into SL5338 to increase the efficiency of electroporation into the SL3261 aroA ($r^+m$)vaccine. For electroporation, cells growing in mid-log phase were harvested and washed in half the initial culture volume of ice-cold water, 1/10 volume of ice-cold glycerol (10%), and finally the cells were resuspended to a concentration of $10^{10}$ cells/ml in ice-cold glycerol (10%). To a pre-chilled cuvette was added a mix of 60 μl cells and 100 ng of plasmid DNA. The cells were pulsed using the Porator from Invitrogen (settings: voltage=1750 μv, capacitance=40 μF, resistance=500). Prewarmed L-broth supplemented with 20 mM glucose was added immediately and the cells grown at 37° C. with gentle shaking for 1–1.5 h. The cells were than plated on L-agar plates containing ampicillin and incubated at 37° C. for 16 h.

SDS-PAGE and Western Blotting

Expression of the TetC fusions was tested by SDS-PAGE and Western blotting. Cells growing in mid-log phase with antibiotic selection were harvested by centrifugation and the proteins fractionated by 10% SDS-PAGE. The proteins were transferred to a nitrocellulose membrane by electroblotting and reacted with either a polyclonal rabbit antiserum directed against TetC or the full length P28 protein. The blots were then probed with goat anti-rabbit-Ig conjugated to horseradish peroxidase (Dako, UK) and developed with 4-chloro-1-naphthol.

Glutathione-aqarose Affinity Purification

Bacterial cells expressing the TetC full length P28 gene fusion were grown to log phase, chilled on ice, and harvested by centrifugation at 2500×g for 15 min at 4° C. The cells were resuspended in 1/15th the original volume of ice-cold phosphate buffered saline (PBS) and lysed by sonication in a MSE Soniprep. The insoluble material was removed by centrifugation and to the supernatant was added 1/6 volume of a 50% slurry of pre-swollen glutathione-agarose beads. (Sigma, UK.). After mixing gently at room temperature for 1 h the beads were collected by centrifugation at 1000×g for 10 sec. The supernatant was discarded and the beads resuspended in 20 volumes of cold PBS-0.5% Triton X-100 and the beads collected again by centrifugation. The washing step was repeated three more times. The fusion protein was eluted by adding 1 volume of 50 mM Tris-HCl, pH 8.0 containing 5.0 mM reduced glutathione (Sigma). After mixing gently for 10 min the beads were pelleted as before and the supernatant removed. The elution step was repeated five more times and the supernatant fractions analysed by SDS-PAGE.

Animals

Female BALB/c mice were purchased from Harlan Olac UK Blackthorn, Bicester, UK, and used when at least 8 weeks of age.

Inoculations and Viable Counting or Organ Homogenates

Bacteria were grown in tryptic soy broth (Oxoid) supplemented with 100 μg/ml ampicillin as required. For intravenous inoculation, stationary cultures were diluted in PBS and animals were given approx. $10^5$ cfu in a lateral tail vein in 0.2 ml. For oral inoculation, bacteria were grown in shaken overnight cultures, concentrated by centrifugation, and animals received approximately $5\times10^9$ cfu in 0.2 ml intragastrically via a gavage tube. The inoculum doses were checked by viable counts on tryptic soy agar.

For viable counts on organ homogenates, groups of 3 mice were sacrificed at intervals, the livers and spleen and (for orally inoculated mice) a pool of mesenteric lymph nodes were homogenised separately in 10 ml distilled water in a Colworth stomacher [C. E. Hormaeche Immunology 37, 311–318, 1979] and viable counts performed on tryptic soy agar supplemented with 100 μg/ml ampicillin.

Measurement of Antibody Responses

Antibodies were measured by solid phase immunoassay. 96-well-flat bottomed plates were coated with either 0.1 μg of TetC (a kind gift from Dr N Fairweather, the Wellcome Foundation, Beckenham UK) or 1 μg of recombinant P28 (a kind gift from Dr R Pierce, Pasteur Institute, Lille, France) in 100 μl of 0.1 M carbonate buffer, pH 9.6. After overnight incubation at 4° C. the plates were incubated for 1 h at 37° C. Blocking of non-specific binding sites was carried out by incubation with 200 μl of 2% casein (BDH, Poole, UK) in PBS pH 7.0 for 1 h at 37° C. Plates were washed three times with 0.05% Tween 20 (Sigma) in PBS with a semiautomatic ELISA washer (Titertek, Flow/ICN, Herts UK). 100 μl of sera from inoculated mice diluted 1:20 in 2% casein was added to each well and the plates were incubated for one hour at 37° C. The plates were washed as above and 100 μl of horse radish peroxidase conjugated goat antimouse immunoglobulins (Dako, Bucks UK), diluted according to the manufacturer's instructions in 2% casein in PBS, was added to each well and incubated for one hour at 37° C. The plates were washed as above and three more washes were given with PBS alone. The plates were developed using 3,3',3,3'-tetramethylbenzidine dihydrochloride (Sigma) according to the manufacturer's instructions using phosphate/citrate buffer, pH 5.0 and 0.02% hydrogen peroxide. The plates were incubated for 10–15 min at 37° C. after which the reaction was stopped with 25 μl 3M $H_2SO_4$ (BDH). The plates were read in an ELISA reader at 450 nm.

Measurement of T-cell Responses

Spleens from mice vaccinated 6 months in advance were removed aseptically and single cell suspensions were prepared by mashing the spleens through a stainless steel sieve with the help of a plastic plunger. Cells were washed once in RPMI1640 medium (Flow/ICN) at 300×g and incubated in Gey's solution to lyse the red cells. White cells were washed twice more as above and resuspended in complete medium, i.e. RPMI1640 supplemented with 100 U/ml penicillin G (Flow/ICN), 100 μg/ml streptomycin (Flow/ICN), $2\times10^{-5}$M B-mercapto-ethanol (Sigma), 1 mM N-(2-hydroxyethyl-piperazine-N'-(2-ethanesulphonic acid) (HEPES) (Flow/ICN) and 10% heat inactivated newborn bovine serum (Northumbria Biolabs, Northumberland, UK). For isolation of T-cells, spleen cells were treated as above and after lysis of red cells the white cells were resuspended in warm (37° C.) RPMI1640 and passed through a Wigzell glass bead column [H. Wigzell, et al Scand. J. Immunol 1: 75–87, 1972].

Cells were plated at $2\times10^6$/ml in a final volume of 200 μl of complete medium in 96-well plates in the presence of the relevant antigens. These were either an alkali-treated whole cell soluble extract of *S. typhimurium* C5 prepared as described in Villarreal et al. [Microbial Pathogenesis 13: 305–315, 1992] at 20 μg/ml final concentration; TetC at 10 μg/ml; recombinant *Schistosoma mansoni* P28 at 50 μg/ml; and *S. mansoni* whole adult worm extract (a kind gift from Dr D Dunne, Cambridge University) at 20 μg/ml. Cells were incubated in a 95% humidity, 5% $CO_2$, 37° C. atmosphere.

Feeder cells for T-cells for animals immunised with SL3261(pTECH1-P28) were obtained from syngeneic BALB/c naive spleens prepared as above. For mice immunised with pTETnir15, feeder cells were obtained from similarly immunised animals. After red cell lysis and two washes with RPMI1640 cells were X-ray irradiated at 2000 rads and washed twice more. These antigen presenting cells were resuspended in complete medium to give a final ratio of 1:1 with T-cells.

IL-2 Production and Assay

T-cell suspensions were plated as above. After two days, 50 μl of supernatant was harvested and added to $1\times10^4$ cells/well CTLL-2(IL-2 dependent) in 50 μl of medium. CTLL-2 cells were obtained from Dr J Ellis, University College, London UK and maintained in RPMI1640 supplemented as above, substituting the newborn bovine serum for foetal bovine serum. After 20 h, 20 μl of MTT at a concentration of 5 mg/ml in PBS were added. MTT transformation was measured as indicated elsewhere [Tada et al. J. Immunol. Methods 93: 157–165, 1986]. results were expressed as the mean of the optical density of triplicates read at 570 nm using a reference filter of 630 nm. Significance was determined by Student's t-test.

BACTERIAL SAMPLE DEPOSITS

*Salmonella typhimurium* strains SL3261-pTECH1, SL3261-pTECH1-P28, SL3261-pTECH2, SL3261-pTECH2-P28 Octamer and PTE79 have been deposited at the National Collection of Type Cultures, 61 Colindale Avenue, London, NW9 SHT, UK, on Jul. 15, 1993 under Deposit Numbers NCTC 12831, NCTC 12833, 12832, 12834 and 12837 respectively.

TABLE 1

DNA SEQUENCES OF OLIGONUCLEOTIDES UTILISED IN THE CONSTRUCTION OF THE TETC-HINGE VECTORS

A). Primer 1. Sense PCR (21mer). (SEQ ID NO: 4)

SacII

5'AAA GAC TCC GCG GGC GAA GTT-3'

TETANUS TOXIN C FRAGMENT SEQ.

B). Primer 2. Anti-Sense PCR Primer (64mer). (SEQ ID NO: 5)

BamHI STOP SpeI Xbal HINGE REGION

5'-CTAT GGA TCC TTA ACT AGT GAT TCT AGA GGG CCC CGG CCC

GTC GTT GGT CCA ACC TTC ATC GGT-3'

TETANUS TOXIN C FRAGMENT SEQ. 3'-END

C). The pTECH2 Linker (SEQ ID NO: 6)

XbaI BamHI EcoRV HindIII SpeI Stop *XBamHI**

5'-CTAGA GGATCC GATATC AAGCTT ACTAGT TAA T-3'

3'-T CCTAGG CTATAG TTCGAA TGATCA ATT ACTAG-5'

*This BamHI recognition sequence is now destroyed.

TABLE 2

T-Cell responses (IL-2/IL-4 production) elicited by alkali treated salmonella whole cell extract (C5NaOH), TetC, *Schistosoma mansoni* whole adult worm antigen (SWA), and recombinant P28 in mice immunised with SL3261 (pTETnir15) or SL3261 (pTECH1.P28).

| Immunising | Stimulating antigen | | | | |
|---|---|---|---|---|---|
| strain | none | C5NaOH | TetC | P28 | SWA |
| SL3261 (pTETnir15) | 2 ± 4 | 67 ± 5 | 41 ± 1 | 0 | 0 |
| SL3261 (pTECH1-P28) | 6 ± 2.6 | 109 ± 10 | 50 ± 8 | 25 ± 8 $p < 0.001$ | 17 ± 6 $p < 0.01$ |

Results expressed as $(A_{570}-A_{630}) \times 1000 \pm$ S.D.

TABLE 3

Ogligonucleotide Sequences for HSV, FMDV, and SIV.

HSV1 gD Gene

PCR Primer 1: (SEQ ID NO: 7)
5'-AATGGATCCAAATATGCCCTGGCGGATGC-3'

PCR Primer 2: (SEQ ID NO: 8)
5'-TTAACTAGTGTTGTTCGGGGTGGCCGGGGGAT-3'

FMDV VP1 Epitope

Oligo 1: (SEQ ID NO: 9)
5'-GATCTAAATACTCTGCTTCTGGTTCTGGTGTTCGTGGTGAC
TTCGGTTCTCTGGCTCCGCGTGTTGCTCGTCAGCTGA-3'

Oligo 2: (SEQ ID NO: 10)
5'-CTAGTCAGCTGACGAGCAACACGCGGAGCCAGAGAACCGAA
GTCACCACGAACACCAGAACCAGAAGCAGAGTATTTA-3

TABLE 3-continued

Ogligonucleotide Sequences for HSV, FMDV, and SIV.

SIV gp120 Epitope

Oligo 1: (SEQ ID NO: 11)
5'-GATCTAACATGACCGGTCTGAAACGTGATAAAACCAAAGAA
TACAACGAAACCTGGTACTCTACCA-3'

Oligo 2: (SEQ ID NO: 12)
5'-CTAGTGGTAGAGTACCAGGTTTCGTTGTATTCTTTGGTTTT
ATCACGTTTCAGACCGGTCATGTTA-3'

Sm P28 Gene

PCR Primer 1: (SEQ ID NO: 13)
5'-TAGTCTAGAATGGCTGGCGAGCATATCAAG-3'

PCR Primer 2: (SEQ ID NO: 14)
5'-TTAGGATCCTTAGAAGGGAGTTGCAGGCCT-3'

Sm P28 Epitope

Oligo 1: (SEQ ID NO: 15)
5'-GATCTAAACCGCAGGAAGAAAAAGAAAAAATCACCAAAGAAA
TCCTGAACGGCAAAA-3'

(SEQ ID NO: 16)
Oligo 2:
5'-CTAGTTTTGCCGTTCAGGATTTCTTTGGTGATTTTTTCTTTTTCT
TCCTGCGGTTTA-3'

What is claimed is:

1. An attenuated bacterium comprising a DNA construct comprising a promoter operably linked to a DNA sequence encoding a first and second immunogeiic polypepies and a hinge region, wherein the attenuated bacterium is viable under anaerobic conditions, wherein the promoter induces expression of operably linked DNA sequences under anaerobic conditions, wherein the DNA sequence encoding the first immunogenic polypeptide and the DNA sequence encoding the second immunogenic polypcptide are linked by a DNA sequence encoding a chain of amino acids defining a hinge region, wherein the first immunogenic polypeptide comprises a tetanus toxin C fragment or an epitope thereof, wherein the second immunogenic polypeptide comprises an immunogenic polypeptide of a pathogenic organism, and wherein the DNA construct provides an enhanced level of expression of said second immunogenic polypeptide in said attenuated bacterium relative to a DNA construct, wherein the DNA sequence encoding the first immunogenic polypeptide and said hinge region are absent.

2. The attenuated bacterium according to claim 1 wherein the promoter is the nirB promoter or a part thereof that promotes expression of an operably linked sequence under anaerobic conditions.

3. The attenuated bacterium according to claim 1 wherein the hinge region comprises proline and/or glycine amino acids.

4. The attenuated bacterium according to claim 1 wherein the second immunogenic polypeptide is an immunogenic polypeptide derived from a parasite.

5. The attenuated bacterium according to claim 1 wherein the second immunogenic polypeptide is derived from the P28 protein of *Schistosoma mansoni.*

6. The attenuated bacterium according to claim 1 wherein the attenuated bacterium is selected from the genus Salmonella.

7. A method of immunizing a host against infection caused by a microorganism, which method comprises administering to the host an effective amount of an attenuated bacterium comprising a DNA construct comprising a promoter operably linked to a DNA sequence encoding first and second immunogenic polypeptides and a hinge region, wherein the attenuated bacterium is viable under anaerobic conditions, wherein the promoter is induced to promote expression of the operably linked DNA sequences under anaerobic conditions, wherein the DNA sequence encoding the first immunogenic polypeptide and the DNA sequence encoding the second immunogenic polypeptide are linked by a DNA sequence encoding a chain of amino acids defining a hinge region, wherein the first immunogenic polypeptide comprises a tetanus toxin C fragment or an epitope thereof, wherein the second immunogenic polypeptide comprises an immunogenic polypeptide of a pathogenic microorganism, and wherein the DNA construct provides an enhanced level of expression of said second immunogenic polypeptide in said attenuated bacterium relative to a DNA construct, wherein the DNA sequence encoding said first immunogenic polypeptide and said hinge region are absent.

8. The method according to claim 7 wherein the host is a human.

9. The method according to claim 7 wherein the promoter is the nirB promoter or a part thereof that promotes expression of an operably linked sequence under anaerobic-conditions.

10. The method according to claim 7 wherein the hinge region comprises proline and/or glycine amino acids.

11. The method according to claim 7, wherein the antigenic determinant is an antigenic sequence derived from a parasite.

12. The method according to claim 7 wherein the second immunogenic sequence is derived from the P28 protein of *Schistosoma mansoni.*

13. The method according to claim 7 wherein the attenuated bacterium is selected from the genus Salmonella.

14. An attenuated Salmonella bacterium comprising a DNA construct comprising a nirB promoter that is induced under anaerobic conditions, the promoter being operably linked to a DNA sequence encoding first and second immunogenic polypeptides linked by a DNA sequence encoding a chain of amino acids defining a hinge region, wherein the first immunogenic polypeptide comprises a tetanus toxin C fragment or an epitope thereof, wherein the second immunogenic polypeptide comprises an immunogenic polypeptide of a pathogenic organism, and wherein the DNA construct provides an enhanced level of expression of said second immunogenic polypeptide in said attenuated bacterium relative to a DNA construct, wherein the DNA sequence encoding said first immunogenic polypeptide and said hinge region are absent.

15. A method of immunizing a host against infection caused by a microorganism, which method comprises administering to the host an effective amount of an attenuated Salmonella bacterium comprising a DNA construct comprising a nirB promoter that is induced under Aerobic conditions, the promoter being operably linked to a DNA sequence encoding first and second immunogenic polypeptides linked by a DNA sequence encoding a chain of amino acids defining a hinge region, wherein the first immunogenic potypeptide comprises a tetanus toxin C fragment or an epitope thereof, and the second polypeptide comprises an immunogenic polypeptide of a pathogenic organism, and wherein the DNA construct provides an enhanced level of expression of said second immunogenic polypeptide in said attenuated bacterium relative to a DNA construct, wherein the DNA sequence encoding said first immunogenic polypeptide and said hinge region are absent.

* * * * *

UNITED STATES PATENT AND TRADEMARK OFFICE

CERTIFICATE OF CORRECTION

PATENT NO. : 6,680,182 B1
DATED : January 20, 2004
INVENTOR(S) : Khan et al.

It is certified that error appears in the above-identified patent and that said Letters Patent is hereby corrected as shown below:

Column 35,
Line 48, delete "immunogeiic polypepies" and replace with -- immunogenic polypeptides --.
Line 57, delete "polypcptide" and replace with -- polypeptide --.

Column 37,
Line 34, delete "sequence" and replace with -- polypeptides --.

Column 38,
Line 22, delete "Aerobic" and replace with -- anaerobic --.
Line 27, delete "potypeptide" and replace with -- polypeptide --.

Signed and Sealed this

Thirtieth Day of March, 2004

JON W. DUDAS
*Acting Director of the United States Patent and Trademark Office*

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
(A) LENGTH: 68 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO (vi) ORIGINAL SOURCE:
(A) ORGANISM: Escherichia coli (ix) FEATURE:
(A) NAME/KEY: promoter
(B) LOCATION: 1..61

(xi) SEQUENCE DESCRIPTION: SEQ ID NO: 1:

AATTCAGGTA AATTTGATGT ACATCAAATG GTACCCCTTG CTGAATCGTT AAGGTAGGCG 60

GTAGGGCC 68

(2) INFORMATION FOR SEQ ID NO: 2:

(i) SEQUENCE CHARACTERISTICS:
(A) LENGTH: 68 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO

```
    (xi) SEQUENCE DESCRIPTION: SEQ ID NO: 2:

AATTCAGGTA AATTTGATGT ACATCAAATG GTACCCCTTG CTGAATCGTT AAGGTAGGCG     60

GTAGGGCC                                                              68


(2) INFORMATION FOR SEQ ID NO: 3:

     (i) SEQUENCE CHARACTERISTICS:
          (A) LENGTH: 60 base pairs
          (B) TYPE: nucleic acid
          (C) STRANDEDNESS: single
          (D) TOPOLOGY: linear

    (ii) MOLECULE TYPE: DNA (genomic)

   (iii) HYPOTHETICAL: NO

   (iii) ANTI-SENSE: NO

    (xi) SEQUENCE DESCRIPTION: SEQ ID NO: 3:

CTACCGCCTA CCTTAACGAT TCAGCAAGGG GTACCATTTG ATGTACATCA AATTTACCTG     60


(2) INFORMATION FOR SEQ ID NO: 4:

     (i) SEQUENCE CHARACTERISTICS:
          (A) LENGTH: 21 base pairs
          (B) TYPE: nucleic acid
          (C) STRANDEDNESS: single
          (D) TOPOLOGY: linear

    (ii) MOLECULE TYPE: DNA (genomic)

   (iii) HYPOTHETICAL: NO

   (iii) ANTI-SENSE: NO

    (xi) SEQUENCE DESCRIPTION: SEQ ID NO: 4:

AAAGACTCCG CGGGCGAAGT T                                               21


(2) INFORMATION FOR SEQ ID NO: 5:

     (i) SEQUENCE CHARACTERISTICS:
          (A) LENGTH: 64 base pairs
          (B) TYPE: nucleic acid
          (C) STRANDEDNESS: single
          (D) TOPOLOGY: linear

    (ii) MOLECULE TYPE: DNA (genomic)

   (iii) HYPOTHETICAL: NO

   (iii) ANTI-SENSE: YES

    (xi) SEQUENCE DESCRIPTION: SEQ ID NO: 5:

CTATGGATCC TTAACTAGTG ATTCTAGAGG GCCCCGGCCC GTCGTTGGTC CAACCTTCAT     60

CGGT                                                                  64


(2) INFORMATION FOR SEQ ID NO: 6:

     (i) SEQUENCE CHARACTERISTICS:
          (A) LENGTH: 33 base pairs
          (B) TYPE: nucleic acid
          (C) STRANDEDNESS: double
          (D) TOPOLOGY: linear

    (ii) MOLECULE TYPE: DNA (genomic)

   (iii) HYPOTHETICAL: NO

   (iii) ANTI-SENSE: NO
```

-continued (xi) SEQUENCE DESCRIPTION: SEQ ID NO: 6:

CTAGAGGATC CGATATCAAG CTTACTAGTT AAT 33

(2) INFORMATION FOR SEQ ID NO: 7:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 7:

AATGGATCCA AATATGCCCT GGCGGATGC 29

(2) INFORMATION FOR SEQ ID NO: 8:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 8:

TAACTAGTGT TGTTCGGGGT GGCCGGGGGA T 31

(2) INFORMATION FOR SEQ ID NO: 9:

(i) SEQUENCE CHARACTERISTICS:
(A) LENGTH: 78 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 9:

GATCTAAATA CTCTGCTTCT GGTTCTGGTG TTCGTGGTGA CTTCGGTTCT CTGGCTCCGC 60

GTGTTGCTCG TCAGCTGA 78

(2) INFORMATION FOR SEQ ID NO: 10:

(i) SEQUENCE CHARACTERISTICS:
(A) LENGTH: 78 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 10:

CTAGTCAGCT GACGAGCAAC ACGCGGAGCC AGAGAACCGA AGTCACCACG AACACCAGAA 60

CCAGAAGCAG AGTATTTA 78

(2) INFORMATION FOR SEQ ID NO: 11:

(i) SEQUENCE CHARACTERISTICS:
(A) LENGTH: 66 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 11:

GATCTAACAT GACCGGTCTG AAACGTGATA AAACCAAAGA ATACAACGAA ACCTGGTACT 60

CTACCA 66

(2) INFORMATION FOR SEQ ID NO: 12:

(i) SEQUENCE CHARACTERISTICS:
(A) LENGTH: 66 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 12:

CTAGTGGTAG AGTACCAGGT TTCGTTGTAT TCTTTGGTTT TATCACGTTT CAGACCGGTC 60

ATGTTA 66

(2) INFORMATION FOR SEQ ID NO: 13:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 13:

TAGTCTAGAA TGGCTGGCGA GCATATCAAG 30

(2) INFORMATION FOR SEQ ID NO: 14:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO

-continued (iii) ANTI-SENSE: NO (xi) SEQUENCE DESCRIPTION: SEQ ID NO: 14:

TTAGGATCCT TAGAAGGGAG TTGCAGGCCT 30

(2) INFORMATION FOR SEQ ID NO: 15:

(i) SEQUENCE CHARACTERISTICS:
(A) LENGTH: 57 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 15:

GATCTAAACC GCAGGAAGAA AAAGAAAAAA TCACCAAAGA AATCCTGAAC GGCAAAA 57

(2) INFORMATION FOR SEQ ID NO: 16:

(i) SEQUENCE CHARACTERISTICS:
(A) LENGTH: 57 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 16:

CTAGTTTTGC CGTTCAGGAT TTCTTTGGTG ATTTTTTCTT TTTCTTCCTG CGGTTTA 57

(2) INFORMATION FOR SEQ ID NO: 17:

(i) SEQUENCE CHARACTERISTICS:
(A) LENGTH: 3754 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iii) ANTI-SENSE: NO (xi) SEQUENCE DESCRIPTION: SEQ ID NO: 17:

TTCAGGTAAA TTTGATGTAC ATCAAATGGT ACCCCTTGCT GAATCGTTAA GGTAGGCGGT 60

AGGGCCCAGA TCTTAATCAT CCACAGGAGA CTTTCTGATG AAAAACCTTG ATTGTTGGGT 120

CGACAACGAA GAAGACATCG ATGTTATCCT GAAAAAGTCT ACCATTCTGA ACTTGGACAT 180

CAACAACGAT ATTATCTCCG ACATCTCTGG TTTCAACTCC TCTGTTATCA CATATCCAGA 240

TGCTCAATTG GTGCCGGGCA TCAACGGCAA AGCTATCCAC CTGGTTAACA ACGAATCTTC 300

TGAAGTTATC GTGCACAAGG CCATGGACAT CGAATACAAC GACATGTTCA ACAACTTCAC 360

CGTTAGCTTC TGGCTGCGCG TTCCGAAAGT TTCTGCTTCC CACCTGGAAC AGTACGGCAC 420

TAACGAGTAC TCCATCATCA GCTCTATGAA GAAACACTCC CTGTCCATCG GCTCTGGTTG 480

GTCTGTTTCC CTGAAGGGTA ACAACCTGAT CTGGACTCTG AAAGACTCCG CGGGCGAAGT 540

-continued

```
TCGTCAGATC ACTTTCCGCG ACCTGCCGGA CAAGTTCAAC GCGTACCTGG CTAACAAATG    600
GGTTTTCATC ACTATCACTA ACGATCGTCT GTCTTCTGCT AACCTGTACA TCAACGGCGT    660
TCTGATGGGC TCCGCTGAAA TCACTGGTCT GGGCGCTATC CGTGAGGACA ACAACATCAC    720
TCTTAAGCTG GACCGTTGCA ACAACAACAA CCAGTACGTA TCCATCGACA AGTTCCGTAT    780
CTTCTGCAAA GCACTGAACC CGAAAGAGAT CGAAAAACTG TATACCAGCT ACCTGTCTAT    840
CACCTTCCTG CGTGACTTCT GGGGTAACCC GCTGCGTTAC GACACCGAAT ATTACCTGAT    900
CCCGGTAGCT TCTAGCTCTA AAGACGTTCA GCTGAAAAAC ATCACTGACT ACATGTACCT    960
GACCAACGCG CCGTCCTACA CTAACGGTAA ACTGAACATC TACTACCGAC GTCTGTACAA   1020
CGGCCTGAAA TTCATCATCA AACGCTACAC TCCGAACAAC GAAATCGATT CTTTCGTTAA   1080
ATCTGGTGAC TTCATCAAAC TGTACGTTTC TTACAACAAC AACGAACACA TCGTTGGTTA   1140
CCCGAAAGAC GGTAACGCTT TCAACAACCT GGACAGAATT CTGCGTGTTG GTTACAACGC   1200
TCCGGGTATC CCGCTGTACA AAAAAATGGA AGCTGTTAAA CTGCGTGACC TGAAAACCTA   1260
CTCTGTTCAG CTGAAACTGT ACGACGACAA AAACGCTTCT CTGGGTCTGG TTGGTACCCA   1320
CAACGGTCAG ATCGGTAACG ACCCGAACCG TGACATCCTG ATCGCTTCTA ACTGGTACTT   1380
CAACCACCTG AAAGACAAAA TCCTGGGTTG CGACTGGTAC TTCGTTCCGA CCGATGAAGG   1440
TTGGACCAAC GACGGGCCGG GGCCCTCTAG AATCACTAGT TAAGGATCCG CTAGCCCGCC   1500
TAATGAGCGG GCTTTTTTTT CTCGGGCAGC GTTGGGTCCT GGCCACGGGT GCGCATGATC   1560
GTGCTCCTGT CGTTGAGGAC CCGGCTAGGC TGGCGGGGTT GCCTTACTGG TTAGCAGAAT   1620
GAATCACCGA TACGCGAGCG AACGTGAAGC GACTGCTGCT GCAAAACGTC TGCGACCTGA   1680
GCAACAACAT GAATGGTCTT CGGTTTCCGT GTTTCGTAAA GTCTGGAAAC GCGGAAGTCA   1740
GCGCTCTTCC GCTTCCTCGC TCACTGACTC GCTGCGCTCG GTCGTTCGGC TGCGGCGAGC   1800
GGTATCAGCT CACTCAAAGG CGGTAATACG GTTATCCACA GAATCAGGGG ATAACGCAGG   1860
AAAGAACATG TGAGCAAAAG GCCAGCAAAA GGCCAGGAAC CGTAAAAAGG CCGCGTTGCT   1920
GGCGTTTTTC CATAGGCTCC GCCCCCCTGA CGAGCATCAC AAAAATCGAC GCTCAAGTCA   1980
GAGGTGGCGA AACCCGACAG GACTATAAAG ATACCAGGCG TTTCCCCCTG GAAGCTCCCT   2040
CGTGCGCTCT CCTGTTCCGA CCCTGCCGCT TACCGGATAC CTGTCCGCCT TTCTCCCTTC   2100
GGGAAGCGTG GCGCTTTCTC AATGCTCACG CTGTAGGTAT CTCAGTTCGG TGTAGGTCGT   2160
TCGCTCCAAG CTGGGCTGTG TGCACGAACC CCCCGTTCAG CCCGACCGCT GCGCCTTATC   2220
CGGTAACTAT CGTCTTGAGT CCAACCCGGT AAGACACGAC TTATCGCCAC TGGCAGCAGC   2280
CACTGGTAAC AGGATTAGCA GAGCGAGGTA TGTAGGCGGT GCTACAGAGT TCTTGAAGTG   2340
GTGGCCTAAC TACGGCTACA CTAGAAGGAC AGTATTTGGT ATCTGCGCTC TGCTGAAGCC   2400
AGTTACCTTC GGAAAAAGAG TTGGTAGCTC TTGATCCGGC AAACAAACCA CCGCTGGTAG   2460
CGGTGGTTTT TTTGTTTGCA AGCAGCAGAT TACGCGCAGA AAAAAAGGAT CTCAAGAAGA   2520
TCCTTTGATC TTTTCTACGG GGTCTGACGC TCAGTGGAAC GAAAACTCAC GTTAAGGGAT   2580
TTTGGTCATG AGATTATCAA AAAGGATCTT CACCTAGATC CTTTTAAATT AAAAATGAAG   2640
TTTTAAATCA ATCTAAAGTA TATATGAGTA AACTTGGTCT GACAGTTACC AATGCTTAAT   2700
CAGTGAGGCA CCTATCTCAG CGATCTGTCT ATTTCGTTCA TCCATAGTTG CCTGACTCCC   2760
CGTCGTGTAG ATAACTACGA TACGGGAGGG CTTACCATCT GGCCCCAGTG CTGCAATGAT   2820
ACCGCGAGAC CCACGCTCAC CGGCTCCAGA TTTATCAGCA ATAAACCAGC CAGCCGGAAG   2880
GGCCGAGCGC AGAAGTGGTC CTGCAACTTT ATCCGCCTCC ATCCAGTCTA TTAATTGTTG   2940
```

-continued

```
CCGGGAAGCT AGAGTAAGTA GTTCGCCAGT TAATAGTTTG CGCAACGTTG TTGCCATTGC   3000
TGCAGGCATC GTGGTGTCAC GCTCGTCGTT TGGTATGGCT TCATTCAGCT CCGGTTCCCA   3060
ACGATCAAGG CGAGTTACAT GATCCCCCAT GTTGTGCAAA AAAGCGGTTA GCTCCTTCGG   3120
TCCTCCGATC GTTGTCAGAA GTAAGTTGGC CGCAGTGTTA TCACTCATGG TTATGGCAGC   3180
ACTGCATAAT TCTCTTACTG TCATGCCATC CGTAAGATGC TTTTCTGTGA CTGGTGAGTA   3240
CTCAACCAAG TCATTCTGAG AATAGTGTAT GCGGCGACCG AGTTGCTCTT GCCCGGCGTC   3300
AACACGGGAT AATACCGCGC CACATAGCAG AACTTTAAAA GTGCTCATCA TTGGAAAACG   3360
TTCTTCGGGG CGAAAACTCT CAAGGATCTT ACCGCTGTTG AGATCCAGTT CGATGTAACC   3420
CACTCGTGCA CCCAACTGAT CTTCAGCATC TTTTACTTTC ACCAGCGTTT CTGGGTGAGC   3480
AAAAACAGGA AGGCAAAATG CCGCAAAAAA GGGAATAAGG GCGACACGGA AATGTTGAAT   3540
ACTCATACTC TTCCTTTTTC AATATTATTG AAGCATTTAT CAGGGTTATT GTCTCATGAG   3600
CGGATACATA TTTGAATGTA TTTAGAAAAA TAAACAAATA GGGGTTCCGC GCACATTTCC   3660
CCGAAAAGTG CCACCTGACG TCTAAGAAAC CATTATTATC ATGACATTAA CCTATAAAAA   3720
TAGGCGTATC ACGAGGCCCT TTCGTCTTCA AGAA                               3754
```

(2) INFORMATION FOR SEQ ID NO: 18:

(i) SEQUENCE CHARACTERISTICS:
(A) LENGTH: 3769 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iii) ANTI-SENSE: NO (xi) SEQUENCE DESCRIPTION: SEQ ID NO: 18:

```
TTCAGGTAAA TTTGATGTAC ATCAAATGGT ACCCCTTGCT GAATCGTTAA GGTAGGCGGT     60
AGGGCCCAGA TCTTAATCAT CCACAGGAGA CTTTCTGATG AAAAACCTTG ATTGTTGGGT    120
CGACAACGAA GAAGACATCG ATGTTATCCT GAAAAAGTCT ACCATTCTGA ACTTGGACAT    180
CAACAACGAT ATTATCTCCG ACATCTCTGG TTTCAACTCC TCTGTTATCA CATATCCAGA    240
TGCTCAATTG GTGCCGGGCA TCAACGGCAA AGCTATCCAC CTGGTTAACA ACGAATCTTC    300
TGAAGTTATC GTGCACAAGG CCATGGACAT CGAATACAAC GACATGTTCA ACAACTTCAC    360
CGTTAGCTTC TGGCTGCGCG TTCCGAAAGT TTCTGCTTCC CACCTGGAAC AGTACGGCAC    420
TAACGAGTAC TCCATCATCA GCTCTATGAA GAAACACTCC CTGTCCATCG GCTCTGGTTG    480
GTCTGTTTCC CTGAAGGGTA ACAACCTGAT CTGGACTCTG AAAGACTCCG CGGGCGAAGT    540
TCGTCAGATC ACTTTCCGCG ACCTGCCGGA CAAGTTCAAC GCGTACCTGG CTAACAAATG    600
GGTTTTCATC ACTATCACTA ACGATCGTCT GTCTTCTGCT AACCTGTACA TCAACGGCGT    660
TCTGATGGGC TCCGCTGAAA TCACTGGTCT GGGCGCTATC CGTGAGGACA ACAACATCAC    720
TCTTAAGCTG GACCGTTGCA ACAACAACAA CCAGTACGTA TCCATCGACA AGTTCCGTAT    780
CTTCTGCAAA GCACTGAACC CGAAAGAGAT CGAAAAACTG TATACCAGCT ACCTGTCTAT    840
CACCTTCCTG CGTGACTTCT GGGGTAACCC GCTGCGTTAC GACACCGAAT ATTACCTGAT    900
CCCGGTAGCT TCTAGCTCTA AAGACGTTCA GCTGAAAAAC ATCACTGACT ACATGTACCT    960
GACCAACGCG CCGTCCTACA CTAACGGTAA ACTGAACATC TACTACCGAC GTCTGTACAA   1020
```

-continued

```
CGGCCTGAAA TTCATCATCA AACGCTACAC TCCGAACAAC GAAATCGATT CTTTCGTTAA   1080

ATCTGGTGAC TTCATCAAAC TGTACGTTTC TTACAACAAC AACGAACACA TCGTTGGTTA   1140

CCCGAAAGAC GGTAACGCTT TCAACAACCT GGACAGAATT CTGCGTGTTG GTTACAACGC   1200

TCCGGGTATC CCGCTGTACA AAAAAATGGA AGCTGTTAAA CTGCGTGACC TGAAAACCTA   1260

CTCTGTTCAG CTGAAACTGT ACGACGACAA AAACGCTTCT CTGGGTCTGG TTGGTACCCA   1320

CAACGGTCAG ATCGGTAACG ACCCGAACCG TGACATCCTG ATCGCTTCTA ACTGGTACTT   1380

CAACCACCTG AAAGACAAAA TCCTGGGTTG CGACTGGTAC TTCGTTCCGA CCGATGAAGG   1440

TTGGACCAAC GACGGGCCGG GGCCCTCTAG AGGATCCGAT ATCAAGCTTA CTAGTTAATG   1500

ATCCGCTAGC CCGCCTAATG AGCGGGCTTT TTTTTCTCGG GCAGCGTTGG GTCCTGGCCA   1560

CGGGTGCGCA TGATCGTGCT CCTGTCGTTG AGGACCCGGC TAGGCTGGCG GGGTTGCCTT   1620

ACTGGTTAGC AGAATGAATC ACCGATACGC GAGCGAACGT GAAGCGACTG CTGCTGCAAA   1680

ACGTCTGCGA CCTGAGCAAC AACATGAATG GTCTTCGGTT TCCGTGTTTC GTAAAGTCTG   1740

GAAACGCGGA AGTCAGCGCT CTTCCGCTTC CTCGCTCACT GACTCGCTGC GCTCGGTCGT   1800

TCGGCTGCGG CGAGCGGTAT CAGCTCACTC AAAGGCGGTA ATACGGTTAT CCACAGAATC   1860

AGGGGATAAC GCAGGAAAGA ACATGTGAGC AAAAGGCCAG CAAAAGGCCA GGAACCGTAA   1920

AAAGGCCGCG TTGCTGGCGT TTTTCCATAG GCTCCGCCCC CCTGACGAGC ATCACAAAAA   1980

TCGACGCTCA AGTCAGAGGT GGCGAAACCC GACAGGACTA TAAAGATACC AGGCGTTTCC   2040

CCCTGGAAGC TCCCTCGTGC GCTCTCCTGT TCCGACCCTG CCGCTTACCG GATACCTGTC   2100

CGCCTTTCTC CCTTCGGGAA GCGTGGCGCT TTCTCAATGC TCACGCTGTA GGTATCTCAG   2160

TTCGGTGTAG GTCGTTCGCT CCAAGCTGGG CTGTGTGCAC GAACCCCCCG TTCAGCCCGA   2220

CCGCTGCGCC TTATCCGGTA ACTATCGTCT TGAGTCCAAC CCGGTAAGAC ACGACTTATC   2280

GCCACTGGCA GCAGCCACTG GTAACAGGAT TAGCAGAGCG AGGTATGTAG GCGGTGCTAC   2340

AGAGTTCTTG AAGTGGTGGC CTAACTACGG CTACACTAGA AGGACAGTAT TTGGTATCTG   2400

CGCTCTGCTG AAGCCAGTTA CCTTCGGAAA AAGAGTTGGT AGCTCTTGAT CCGGCAAACA   2460

AACCACCGCT GGTAGCGGTG GTTTTTTTGT TTGCAAGCAG CAGATTACGC GCAGAAAAAA   2520

AGGATCTCAA GAAGATCCTT TGATCTTTTC TACGGGGTCT GACGCTCAGT GGAACGAAAA   2580

CTCACGTTAA GGGATTTTGG TCATGAGATT ATCAAAAAGG ATCTTCACCT AGATCCTTTT   2640

AAATTAAAAA TGAAGTTTTA AATCAATCTA AAGTATATAT GAGTAAACTT GGTCTGACAG   2700

TTACCAATGC TTAATCAGTG AGGCACCTAT CTCAGCGATC TGTCTATTTC GTTCATCCAT   2760

AGTTGCCTGA CTCCCCGTCG TGTAGATAAC TACGATACGG GAGGGCTTAC CATCTGGCCC   2820

CAGTGCTGCA ATGATACCGC GAGACCCACG CTCACCGGCT CCAGATTTAT CAGCAATAAA   2880

CCAGCCAGCC GGAAGGGCCG AGCGCAGAAG TGGTCCTGCA ACTTTATCCG CCTCCATCCA   2940

GTCTATTAAT TGTTGCCGGG AAGCTAGAGT AAGTAGTTCG CCAGTTAATA GTTTGCGCAA   3000

CGTTGTTGCC ATTGCTGCAG GCATCGTGGT GTCACGCTCG TCGTTTGGTA TGGCTTCATT   3060

CAGCTCCGGT TCCCAACGAT CAAGGCGAGT TACATGATCC CCCATGTTGT GCAAAAAAGC   3120

GGTTAGCTCC TTCGGTCCTC CGATCGTTGT CAGAAGTAAG TTGGCCGCAG TGTTATCACT   3180

CATGGTTATG GCAGCACTGC ATAATTCTCT TACTGTCATG CCATCCGTAA GATGCTTTTC   3240

TGTGACTGGT GAGTACTCAA CCAAGTCATT CTGAGAATAG TGTATGCGGC GACCGAGTTG   3300

CTCTTGCCCG GCGTCAACAC GGGATAATAC CGCGCCACAT AGCAGAACTT TAAAAGTGCT   3360

CATCATTGGA AAACGTTCTT CGGGGCGAAA ACTCTCAAGG ATCTTACCGC TGTTGAGATC   3420
```

-continued

```
CAGTTCGATG TAACCCACTC GTGCACCCAA CTGATCTTCA GCATCTTTTA CTTTCACCAG   3480

CGTTTCTGGG TGAGCAAAAA CAGGAAGGCA AAATGCCGCA AAAAAGGGAA TAAGGGCGAC   3540

ACGGAAATGT TGAATACTCA TACTCTTCCT TTTTCAATAT TATTGAAGCA TTTATCAGGG   3600

TTATTGTCTC ATGAGCGGAT ACATATTTGA ATGTATTTAG AAAAATAAAC AAATAGGGGT   3660

TCCGCGCACA TTTCCCCGAA AAGTGCCACC TGACGTCTAA GAAACCATTA TTATCATGAC   3720

ATTAACCTAT AAAAATAGGC GTATCACGAG GCCCTTTCGT CTTCAAGAA              3769


(2) INFORMATION FOR SEQ ID NO: 19:

     (i) SEQUENCE CHARACTERISTICS:
          (A) LENGTH: 38 base pairs
          (B) TYPE: nucleic acid
          (C) STRANDEDNESS: double
          (D) TOPOLOGY: circular

    (ii) MOLECULE TYPE: DNA (genomic)

   (iii) HYPOTHETICAL: NO

   (iii) ANTI-SENSE: NO

     (v) FRAGMENT TYPE: internal

    (xi) SEQUENCE DESCRIPTION: SEQ ID NO: 19:

TCTAGAGGAT CCGATATCAA GCTTACTAGT TAATGATC                            38


(2) INFORMATION FOR SEQ ID NO: 20:

     (i) SEQUENCE CHARACTERISTICS:
          (A) LENGTH: 14 amino acids
          (B) TYPE: amino acid
          (D) TOPOLOGY: circular

    (ii) MOLECULE TYPE: peptide

     (v) FRAGMENT TYPE: internal

    (xi) SEQUENCE DESCRIPTION: SEQ ID NO: 20:

Gly Pro Gly Pro Ser Arg Gly Ser Asp Ile Lys Leu Thr Ser
1               5                   10
```